(12) United States Patent
Wong

(10) Patent No.: US 8,680,255 B2
(45) Date of Patent: Mar. 25, 2014

(54) DETECTION OF HBX/8P11 HYBRID SEQUENCE IN HUMAN HEPATOCELLULAR CARCINOMA

(75) Inventor: Nathalie Wong, Hong Kong (CN)

(73) Assignee: The Chinese University of Hong Kong, Shatin, Hong Kong N.T. (CN)

( * ) Notice: Subject to any disclaimer, the term of this patent is extended or adjusted under 35 U.S.C. 154(b) by 0 days.

(21) Appl. No.: 13/599,741

(22) Filed: Aug. 30, 2012

(65) Prior Publication Data

US 2013/0072544 A1 Mar. 21, 2013

Related U.S. Application Data

(60) Provisional application No. 61/530,223, filed on Sep. 1, 2011.

(51) Int. Cl.
*C12Q 1/68* (2006.01)

(52) U.S. Cl.
USPC .............................. 536/23.1; 536/23; 536/24

(58) Field of Classification Search
None
See application file for complete search history.

(56) References Cited

PUBLICATIONS

Lee et al. (Characterization of De Novo Genomic Alterations in HBV-Producing Hepatoma Cells Using Array Comparative Genomic Hybridization, Journal of Cancer Molecules 1(2): 93-98, 2005).*
NCBI Accession NOS FJ62258 (Feb. 3, 2009) & AC015649 (Mar. 16, 2001).*
Didenko (DNA Probes Using Fluorescence Resonance Energy Transfer (FRET): Designs and Applications, Biotechniques, Nov. 2001; 31(5): 1106-1121).*
Ma (Promoter Fusions to Study Gene Expression, in Encyclopedia of Life Sciences, 2007, John Wiley & Sons).*
Buck et al. (Biotechniques. 1999. 27(3): pp. 528-536).*
Lowe et al. (Nucleic Acids Research, vol. 18, No. 7, p. 1757-1761, 1990).*
Stratagene ("Gene Characterization Kits" 1988).*

* cited by examiner

*Primary Examiner* — Christopher M Babic
*Assistant Examiner* — Aaron Priest
(74) *Attorney, Agent, or Firm* — Kilpatrick Townsend & Stockton LLP

(57) ABSTRACT

The present invention provides a method for diagnosing a particular type of human hepatocellular carcinoma (HCC), HBx/8p11-positive HCC, in a subject by detecting the presence of a specific, non-naturally occurring polynucleotide sequence that indicates integration of a portion of the human hepatitis B virus (HBV) sequence into the human genome on chromosome 8 in the 8p11 integration region. A kit and device useful for such a method are also provided. In addition, the present invention provides a method for treating an HBx/8p11-positive HCC.

6 Claims, 12 Drawing Sheets

Figure 1  DNA sequencing of HBx/8p11 integration site in HKCI-4 (upper panel) and H210T (lower panel). Microhomology sequence GTG between HBx and 8p11 was boxed.

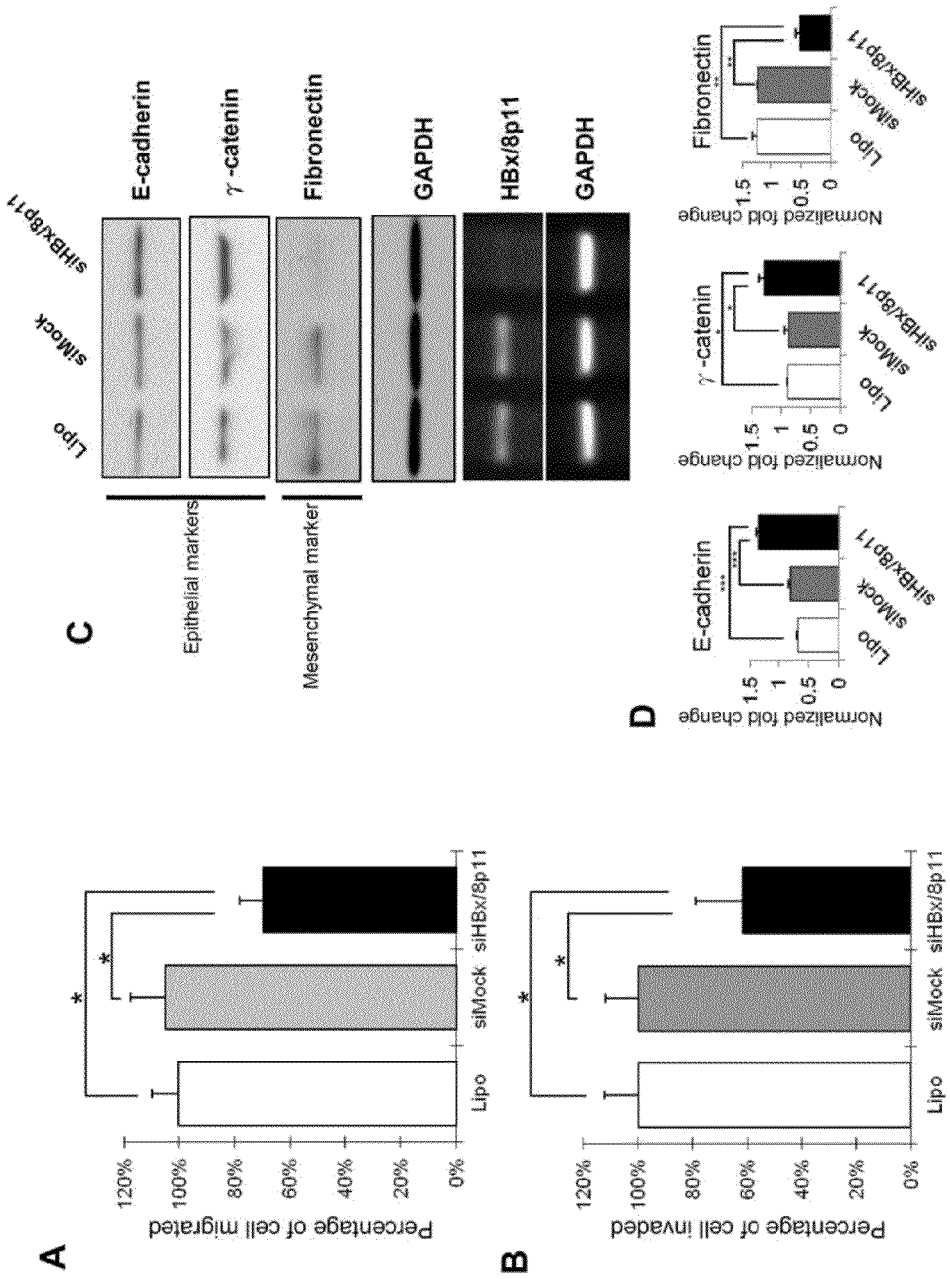
*Figure 4A-D*

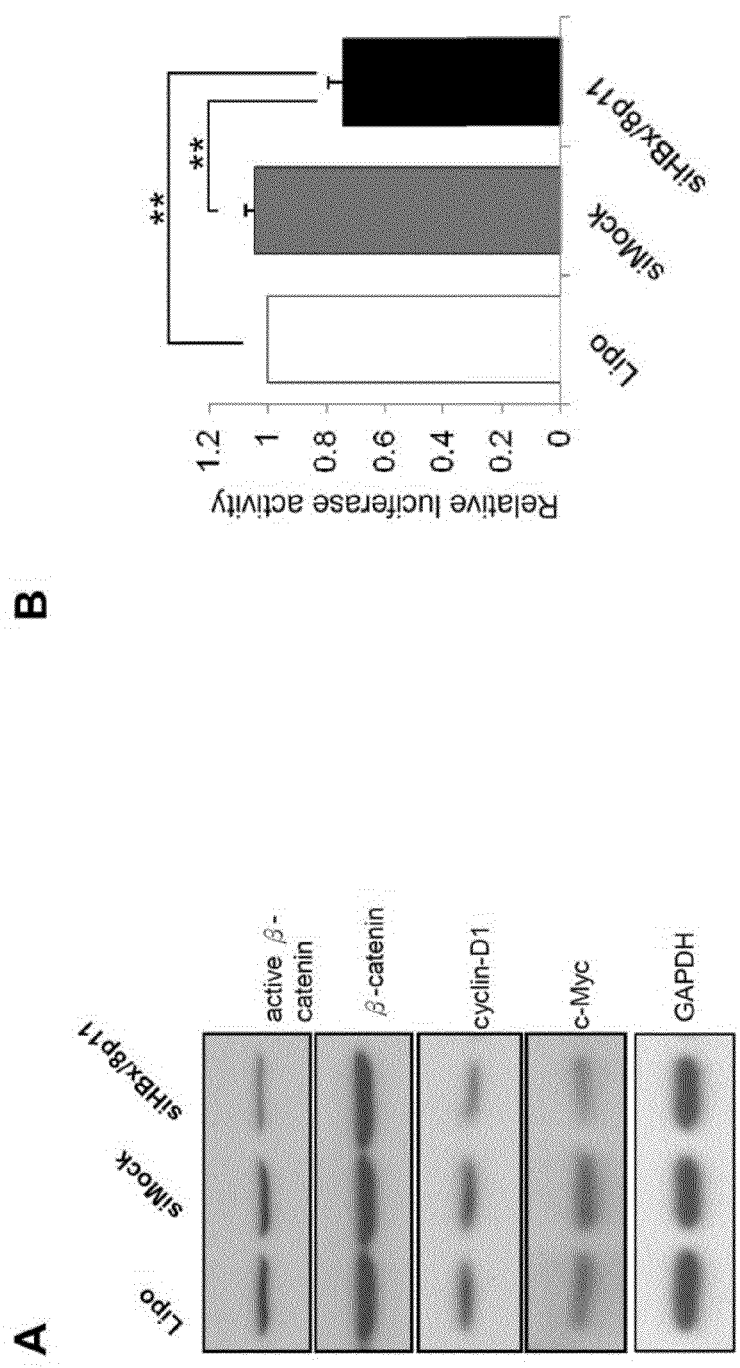
Figure 5A-B

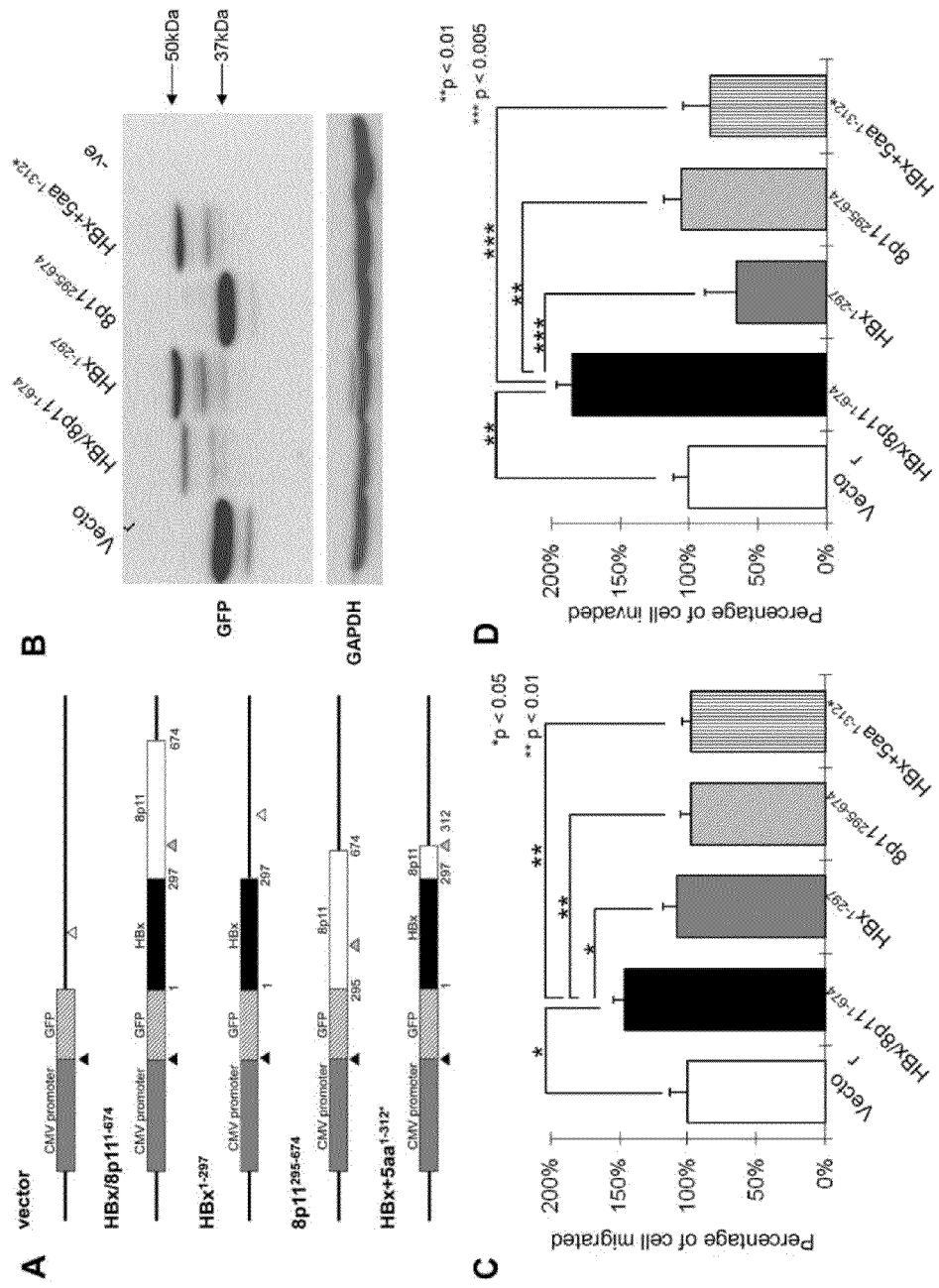
*Figure 6A-D*

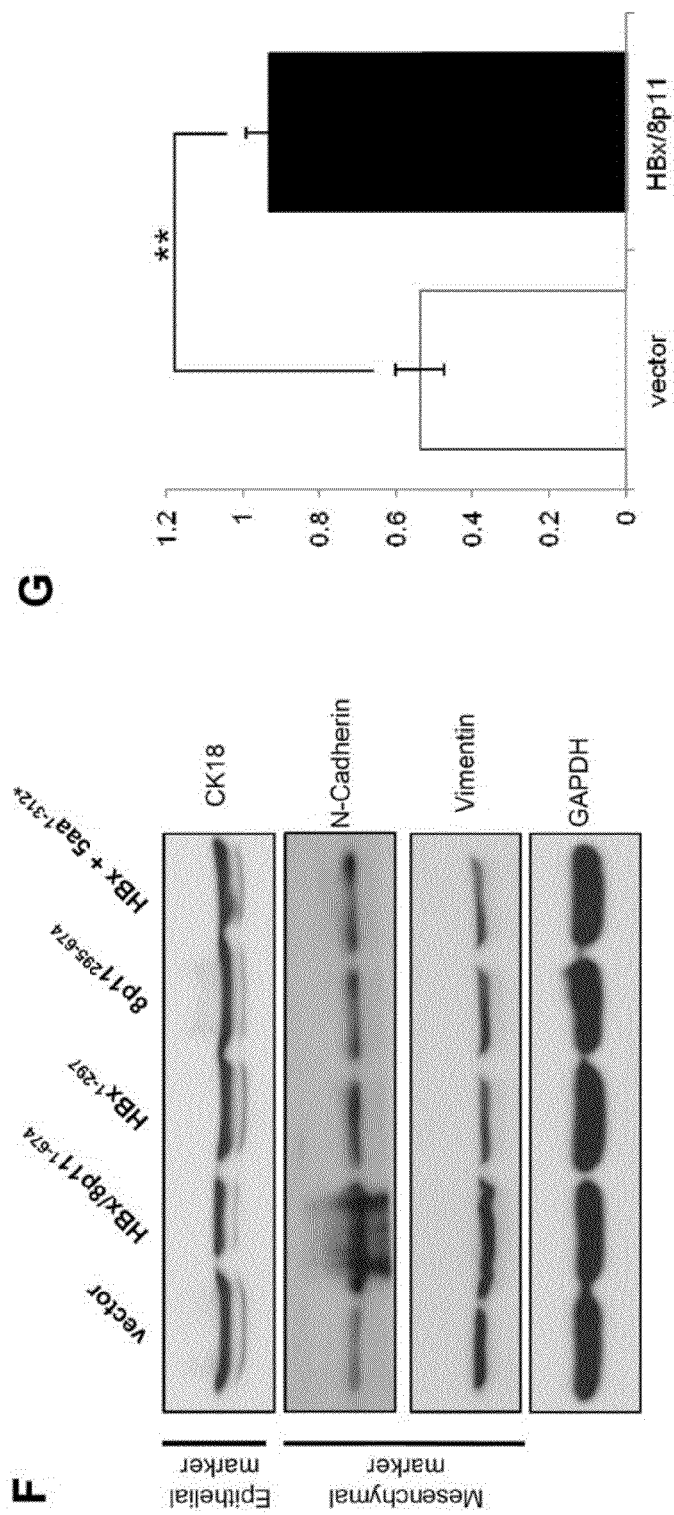
*Figure 6F-G*

SEQUENCE LISTING

<160> NUMBER OF SEQ ID NOS: 16

<210> SEQ ID NO 1
<211> LENGTH: 297
<212> TYPE: DNA
<213> ORGANISM: Artificial Sequence
<220> FEATURE:
<223> OTHER INFORMATION: synthetic polynucleotide sequence corresponding
      to nucleotide positions 1326-1622 of human hepatitis B virus (HBV)

<400> SEQUENCE: 1
cggaaccgac aactctgttg tcctctctcg gaaatacacc tcctttccat ggctgctagg      60
gtgtgctgcc aactggatcc tgcgcgggac gtcctttgtc tacgtcccgt cggcgctgaa    120
tcccgcggac gacccgtctc ggggccgttt gggactctac cgtcccttc ttcgtctgcc     180 gttccggccg accacggggc gcacctctct ttacgcggtc tccccgtctg tgccttctca    240
tctgccggac cgtgtgcact tcgcttcacc tctgcacgtc gcatggaaac caccgtg       297

<210> SEQ ID NO 2
<211> LENGTH: 401
<212> TYPE: DNA
<213> ORGANISM: Homo sapiens
<220> FEATURE:
<223> OTHER INFORMATION: human genomic sequence at 8p11 region,
      nucleotide positions 41,612,680 to 41,613,080

<400> SEQUENCE: 2
atacaaaaat tagacgggca tagtggcggg tgcctgtagt cccagctact cgggaggctg      60
aggcaggaga attgcttgag cctgggaggc agaggttgca gtgagctgag attgcaccac    120
tgcactctgg cctgggtgac agaacgagac tctgtctcag gaaacaaaac aaaacaaaaa    180
ccccaaaaac aaatcaaaca cttcgatagc aagaaaacaa ataacccaat taaaaaatgg    240
gcctgggacg tgaatagaca tttctgaaaa taagacatac aaatgaccaa cagacatgaa    300
aaaacaatgc tccacctcac taatcattag ggaatgcaaa ttaaaaccac aatgagctat    360
cgcctcgcac ctgtcagaat gactgttatc aaaaatgcaa g                        401

<210> SEQ ID NO 3
<211> LENGTH: 380
<212> TYPE: DNA
<213> ORGANISM: Homo sapiens
<220> FEATURE:
<223> OTHER INFORMATION: human genomic sequence at 8p11 region,
      nucleotide positions 41,613,080 to 41,613,459

<400> SEQUENCE: 3
gtgttgttga ggatgtgaag taaagaaaac ccttgcctgc tcttggtagg aatgtaaatt      60

```
agattagcta ttgtggaaaa cagcatggag attcctaaaa ctaaaaccag agcttccata    120
tgatccagca gtcccctact aggaaaggaa atcaatatat caaagagata cctgcactcc    180
catgtttatt gcagcactat tcacaatgac caagatttgg aatcaacttg tgtccatcat    240
agatgagtag ataaggaaaa tgtggtatat gtcatcatgg aatattattc ggtgttaaaa    300
aagaaggaaa tcctgtcatt tgcgacatcg tggatggaat cgaagaacat tatgctaagt    360
aaaataaatc aatcacagga                                                380
```

<210> SEQ ID NO 4
<211> LENGTH: 674
<212> TYPE: DNA
<213> ORGANISM: Unknown
<220> FEATURE:
<223> OTHER INFORMATION: HBx/8p11 coding sequence, full-length HBx/8p11
      fusion transcript encompassing part of HBx open reading frame and
      intergenic sequence from 8p11, chimeric transcript of HBV-human
      chromosome 8 fusion, viral-human chimeric non-coding RNA (ncRNA)
      transcript

<400> SEQUENCE: 4

```
cggaaccgac aactctgttg tcctctctcg gaaatacacc tcctttccat ggctgctagg    60
gtgtgctgcc aactggatcc tgcgcgggac gtcctttgtc tacgtcccgt cggcgctgaa   120
tcccgcggac gacccgtctc ggggccgttt gggactctac cgtcccctte ttcgtctgcc   180 gttccggccg accacggggc gcacctctct ttacgcggtc tccccgtctg tgccttctca   240
tctgccggac cgtgtgcact tcgcttcacc tctgcacgtc gcatggaaac caccgtgttg   300
ttgaggatgt gaagtaaaga aaacccttgc ctgctcttgg taggaatgta aattagatta   360
gctattgtgg aaaacagcat ggagattcct aaaactaaaa ccagagcttc catatgatcc   420
agcagtcccc tactaggaaa ggaaatcaat atatcaaaga gatacctgca ctcccatgtt   480
tattgcagca ctattcacaa tgaccaagat ttggaatcaa cttgtgtcca tcatagatga   540
gtagataagg aaaatgtggt atatgtcatc atggaatatt attcggtgtt aaaaaagaag   600
gaaatcctgt catttgcgac atcgtggatg gaatcgaaga acattatgct aagtaaaata   660
aatcaatcac agga                                                    674
```

<210> SEQ ID NO 5
<211> LENGTH: 25
<212> TYPE: RNA
<213> ORGANISM: Artificial Sequence
<220> FEATURE:
<223> OTHER INFORMATION: synthetic oligonucleotide targeting the
      flanking junction of viral-human HBx/8p11 transcript, siHBx/8p11
      anti-sense RNA

<400> SEQUENCE: 5

```
accaccgugu uguugaggau gugaa                                          25
```

<210> SEQ ID NO 6
<211> LENGTH: 25
<212> TYPE: DNA
<213> ORGANISM: Artificial Sequence
<220> FEATURE:
<223> OTHER INFORMATION: synthetic oligonucleotide targeting the
      flanking junction of viral-human HBx/8p11 transcript, siHBx/8p11
      anti-sense DNA

<400> SEQUENCE: 6

```
accaccgtgt tgttgaggat gtgaa                                          25
```

```
<210> SEQ ID NO 7
<211> LENGTH: 72
<212> TYPE: DNA
<213> ORGANISM: Artificial Sequence
<220> FEATURE:
<223> OTHER INFORMATION: synthetic HBx/8p11 integration site in HKCI-4
      and H210T cell lines

<400> SEQUENCE: 7
tcgcttcacc tctgcacgtc gcatggaaac caccgtgttg ttgaggatgt gaagtaaaga        60
aaacccttgc ct                                                            72

<210> SEQ ID NO 8
<211> LENGTH: 87
<212> TYPE: PRT
<213> ORGANISM: Unknown
<220> FEATURE:
<223> OTHER INFORMATION: translation of full-length HBx/8p11 fusion
      transcript encompassing part of HBx open reading frame and
      intergenic sequence from 8p11, translation of chimeric transcript
      of HBV-human chromosome 8 fusion

<400> SEQUENCE: 8

Met Ala Ala Arg Val Cys Cys Gln Leu Asp Pro Ala Arg Asp Val Leu
 1               5                  10                  15

Cys Leu Arg Pro Val Gly Ala Glu Ser Arg Gly Arg Pro Val Ser Gly
            20                  25                  30

Pro Phe Gly Thr Leu Pro Ser Pro Ser Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Leu Leu Arg Met
                85

<210> SEQ ID NO 9
<211> LENGTH: 21
<212> TYPE: DNA
<213> ORGANISM: Artificial Sequence
<220> FEATURE:
<223> OTHER INFORMATION: synthetic HBV specific amplification primer for
      rapid amplification of cDNA ends (3'-RACE)

<400> SEQUENCE: 9
tgctgccaac tggatcctgc g                                                  21

<210> SEQ ID NO 10
<211> LENGTH: 23
<212> TYPE: DNA
<213> ORGANISM: Artificial Sequence
<220> FEATURE:
<223> OTHER INFORMATION: synthetic HBV-specific primer for nested PCR

<400> SEQUENCE: 10
acgtcctttg tttacgtccc gtc                                                23

<210> SEQ ID NO 11
<211> LENGTH: 21
<212> TYPE: DNA
<213> ORGANISM: Artificial Sequence
<220> FEATURE:
<223> OTHER INFORMATION: synthetic human specific amplification primer
      for rapid amplification of cDNA ends (5'-RACE)

<400> SEQUENCE: 11
```

```
tgctgccaac tggatcctgc g                                        21

<210> SEQ ID NO 12
<211> LENGTH: 20
<212> TYPE: DNA
<213> ORGANISM: Artificial Sequence
<220> FEATURE:
<223> OTHER INFORMATION: synthetic human-specific primer for second
      nested PCR

<400> SEQUENCE: 12
attcctacca agagcaggca                                          20

<210> SEQ ID NO 13
<211> LENGTH: 20
<212> TYPE: DNA
<213> ORGANISM: Artificial Sequence
<220> FEATURE:
<223> OTHER INFORMATION: synthetic amplification primer for first round
      hemi-nested PCR

<400> SEQUENCE: 13
ggactctacc gtcccttct                                           20

<210> SEQ ID NO 14
<211> LENGTH: 20
<212> TYPE: DNA
<213> ORGANISM: Artificial Sequence
<220> FEATURE:
<223> OTHER INFORMATION: synthetic amplification primer for first round
      hemi-nested PCR

<400> SEQUENCE: 14
agtaggggac tgctggatca                                          20

<210> SEQ ID NO 15
<211> LENGTH: 20
<212> TYPE: DNA
<213> ORGANISM: Artificial Sequence
<220> FEATURE:
<223> OTHER INFORMATION: synthetic amplification primer for second round
      hemi-nested PCR

<400> SEQUENCE: 15
ccgtctgtgc cttctcatct                                          20

<210> SEQ ID NO 16
<211> LENGTH: 20
<212> TYPE: DNA
<213> ORGANISM: Artificial Sequence
<220> FEATURE:
<223> OTHER INFORMATION: synthetic amplification primer for second round
      hemi-nested PCR

<400> SEQUENCE: 16
agtaggggac tgctggatca                                          20
```

DETECTION OF HBX/8P11 HYBRID SEQUENCE IN HUMAN HEPATOCELLULAR CARCINOMA

RELATED APPLICATIONS

This application claims priority to U.S. Provisional Patent Application No. 61/530,223, filed Sep. 1, 2011, the contents of which are incorporated by reference in the entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -93-1.TXT, created on Oct. 3, 2012, 8,192 bytes, machine format IBM-PC, MS-Windows operating system, is hereby incorporated by reference in its entirety for all purposes.

BACKGROUND OF THE INVENTION

Hepatocellular carcinoma (HCC) is the most common form of liver cancer and also one of the most common tumors worldwide. Most cases of HCC are secondary to either a viral infection (hepatitis B or C) or cirrhosis (alcoholism being the most common cause of hepatic cirrhosis). In certain regions of the world, such as sub-Saharan Africa and Southeast Asia, HCC is the most common cancer, generally affecting men more than women, and with an age of onset between late teens and 30s. This variability is in part due to the different patterns of hepatitis B and hepatitis C transmission in different populations—infection at or around birth predispose to earlier cancers than if people are infected later. The time interval between hepatitis B virus (HBV) infection and development into HCC can be years, even decades, but from diagnosis of HCC to death the average survival period is several months only. HCC is one of the deadliest cancers in China where chronic hepatitis B is found in 90% of cases. Because of the prevalence of this disease and its grave implications on patients' life expectancy, there exists a need for new methods to diagnose and treat HCC. This invention fulfills this and other related needs.

BRIEF SUMMARY OF THE INVENTION

In one aspect, the present invention provides a method for assessing the presence or risk of HBx/8p11-positive human hepatocellular carcinoma (HCC) in a subject. The method includes the step of detecting, in a biological sample taken from the subject, a polynucleotide sequence comprising SEQ ID NO:1 or complement of SEQ ID NO:1. The presence of the polynucleotide sequence indicates that the subject has HBx/8p11-positive HCC or is at risk of developing HBx/8p11-positive HCC, allowing the diagnosis to be made that either the subject has HBx/8p11-positive HCC or is at risk of developing HBx/8p11-positive HCC, further allowing the attending physician to take therapeutic measures (typically after the diagnosis is confirmed by at least another diagnostic method), such as conventional therapies for treating HCC (e.g., surgical resection, chemotherapy, radiation therapy, high intensity focused ultrasound (HIFU) therapy, cryosurgery, or hormonal therapy), or preventive and/or monitoring measures (typically after confirmation by at least another diagnostic method that HCC is not yet present), such as reduction/avoidance of alcohol consumption, regular medical surveillance utilizing techniques including ultrasound, MRI, and CT scan.

In some cases, the sample used in the claimed method is a liver tissue sample, especially a sample taken from a suspected or confirmed liver tumor site. The polynucleotide sequence being analyzed may be a DNA sequence or an RNA sequence. In one example, the RNA has the nucleotide sequence set forth in SEQ ID NO:4.

In some embodiments, the detecting step in this method comprises an amplification reaction, such as a polymerase chain reaction (PCR), especially a reverse transcriptase-PCR (RT-PCR). In some cases, two oligonucleotide primers are used in the amplification reaction, and the two primers hybridize with (1) SEQ ID NO:2 and SEQ ID NO:3, respectively; or (2) complement of SEQ ID NO:2 and complement of SEQ ID NO:3, respectively. In other cases, the detecting step in this method comprises a polynucleotide hybridization assay, such as a Southern Blot analysis, or a Northern Blot analysis, or an in situ hybridization assay. In some cases, a polynucleotide probe is used in the polynucleotide hybridization assay to hybridize with SEQ ID NO:1 or complement of SEQ ID NO:1. The polynucleotide probe often comprises or is attached to a detectable moiety.

In some embodiments, the test subject in this method has been previously diagnosed with HCC, and presence of the polynucleotide sequence being tested for indicates that the subject has HBx/8p11-positive HCC. In other embodiments, the subject was not previously diagnosed with HCC, and presence of the polynucleotide sequence indicates that the subject is at risk of developing HBx/8p11-positive HCC. In some cases, the detecting step of the method further comprises a polynucleotide hybridization assay using a polynucleotide probe that hybridizes with SEQ ID NO:1 or complement of SEQ ID NO:1.

In another aspect, the present invention provides a kit for assessing the presence or risk of HBx/8p11-positive human hepatocellular carcinoma (HCC) in a subject. The kit includes a polynucleotide probe that (1) hybridizes to SEQ ID NO:1 or complement of SEQ ID NO:1; or (2) hybridizes to SEQ ID NO:4 or complement of SEQ ID NO:4. The polynucleotide probe often comprises or is attached to a detectable moiety. The kit in some cases further includes two oligonucleotide primers, which hybridize with (1) SEQ ID NO:2 and SEQ ID NO:3, respectively; or (2) complement of SEQ ID NO:2 and complement of SEQ ID NO:3, respectively. Typically, the kit will also include an instruction manual, directing the user on how to properly utilize the kit components and interpret results for the intended purposes.

In yet another aspect, the present invention provides a method for treating HBx/8p11-positive human hepatocellular carcinoma (HCC) in a subject. The method comprises the step of administering to the subject an effective amount of a nucleic acid comprising a sequence complementary to at least a portion of SEQ ID NO:1, 3, or 4. For example, the nucleic acid comprises the sequence set forth in SEQ ID NO:5, or the nucleic acid consists of the sequence set forth in SEQ ID NO:5 or 6. In some cases, the nucleic acid is an expression cassette comprising a promoter operably linked to a polynucleotide sequence encoding the sequence complementary to at least a portion of SEQ ID NO:1, 3, or 4. For example, the nucleic acid is an expression cassette comprising a promoter operably linked to a polynucleotide sequence encoding SEQ ID NO:5. A variety of promoters may be used in the expression cassette, for example, the promoter may be a live-specific promoter.

DEFINITIONS

Figure 1:
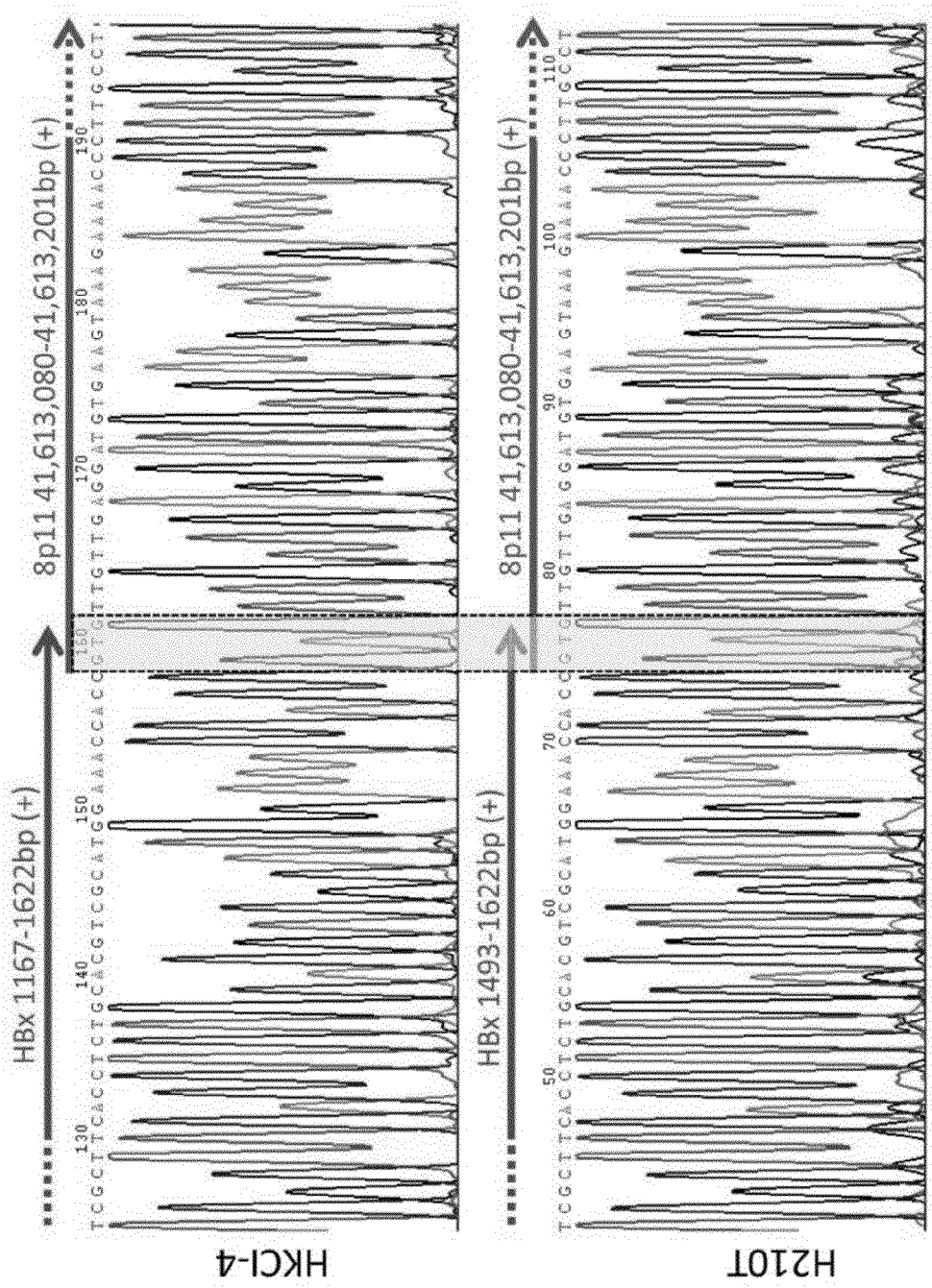
FIG. 1: DNA sequencing of HBx/8p11 integration site in HKCI-4 (upper panel; SEQ ID NO:7) and H210T (lower panel; SEQ ID NO:7). Microhomology sequence GTG between HBx and 8p11 was boxed.

The term "HBx/8p11-positive hepatocellular carcinoma (HCC)," as used in this application, refers to a type of hepatocellular carcinoma (HCC) in which, due to infection by the human hepatitis B virus (HBV), a segment of the HBV DNA sequence is inserted into the human genome on chromosome 8 in the region of p11, resulting in a fusion polynucleotide sequence containing a sequence of HBV origin flanked at two ends by the 8p11 region genomic sequences. SEQ ID NO:4 is the polynucleotide sequence for an exemplary mRNA transcribed from such an HBx/8p11 fusion DNA sequence.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in this application, an "increase" or a "decrease" refers to a detectable positive or negative change in quantity from a comparison basis, e.g., an established baseline value of the level of an mRNA comprising the sequence of SEQ ID NO:1. An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the fusion sequence of HBx/8p11 or a portion thereof. Typically at least one of the PCR primers for amplification of a polynucleotide sequence is sequence-specific for that polynucleotide sequence.

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

The term "treat" or "treating," as used in this application, refers to an act that leads to the elimination, reduction, alleviation, reversal, or prevention or delay of onset or recurrence of any symptom of a relevant condition, such as HBx/8p11-positive HCC. In other words, the act of "treating" a condition encompasses both therapeutic and prophylactic intervention directed to the condition.

The term "amount" as used in this application refers to the quantity of a polynucleotide of interest or a polypeptide of interest, e.g., an mRNA comprising the nucleotide sequence of SEQ ID NO:1. Such quantity may be expressed in the absolute terms, i.e., the total quantity of the polynucleotide or polypeptide in the sample, or in the relative terms, i.e., the concentration of the polynucleotide or polypeptide in the sample.

The term "effective amount" as used herein refers to an amount of a given substance that is sufficient in quantity to produce a desired effect. For example, an effective amount of an antisense oligonucleotide targeting any portion of an mRNA comprising the sequence of SEQ ID NO:1 is the amount of said antisense to achieve a decrease or reduction of the mRNA level, such that the symptoms of HBx/8p11-positive HCC are reduced, reversed, eliminated, or prevented in a patient who has been given the antisense for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, HCC (especially HBx/8p11-positive HCC). Subjects also include individuals currently undergoing therapy that seek manipulation of the therapeutic regimen. Subjects or individuals in need of treatment include those that demonstrate symptoms of HCC or are at risk of suffering from its symptoms. For example, subjects in need of treatment include individuals with a genetic predisposition or family history for HCC, those that have had relevant symptoms in the past, those that have been exposed to a triggering substance or event, as well as those suffering from chronic or acute symptoms of the condition. A "subject in need of treatment" may be at any age of life.

DETAILED DESCRIPTION OF THE INVENTION

I. Introduction

Hepatocellular carcinoma (HCC) is the 5th most common cancer worldwide and a malignancy that is commonly fatal. Chronic hepatitis B virus (HBV) infection is a strong predisposing factor in the development of HCC. It is known that the viral DNA commonly inserts into the genome of HCC patients, although the role of these integrants in the liver carcinogenesis remains largely unclear. In an effort to gain insights into the viral insertional events, the inventor previously examined 15 HCC cell lines and 50 primary tumors that were derived from chronic carriers of HBV. The high-throughput analysis of restriction site-PCR was employed with specific primers designed on the conserved regions of HBV. Alignment of integrants suggested the sites of viral insertion within the vicinity of many important cancer-related genes, including CDH11, MLL4, and MMP4. Of interest, one recurrent flanking sequence of HBx juxtapose to regional chr.8p11 was suggested. By rapid amplification of cDNA ends (RACE) cloning, the inventor further identified chimeric transcription of HBx together with sequence at chromosome 8p11 as a novel fusion product. Preliminary examinations of this chimeric sequence HBV/8p11 in HCC tumors suggested an occurrence of ~36% (19/53 cases), signifying this integration may be a non-random event. Further investigations of HBV/8p11 by transfection assays into immortalized human hepatocyte cell line LO2 suggested functional advantages on cellular proliferation (P<0.05) and augmentation of cell migration (P<0.05).

The present inventor discovered for the first time a high prevalence of HBV/8p11 transcript in HCC tumors. The identification of this novel hybrid HBx/8p11 transcript and the illustration of its significant functional effects provides important means for classification of this particular subset of HCC and treatment of such HCC cases.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the HBx/8p11 fusion, and synthetic oligonucleotides (e.g., primers) can be verified using, e.g., the chain termination method for sequencing double-stranded templates of Wallace et al., *Gene* 16: 21-26 (1981).

III. Acquisition of Tissue Samples and Analysis of Nucleic Acids

The present invention relates to detecting the presence and quantifying the amount of an mRNA that is characteristic of an HBx/8p11-positive HCC in a person's biological sample, such as liver tissue sample, especially one taken from a liver tumor (e.g., biopsy), as a means to detect the presence, to assess the risk of developing, and/or to monitor the progress of the HBx/8p11-positive HCC. Thus, the first steps of practicing this invention are to obtain a biological sample from a test subject and extract mRNA from the sample.

A. Acquisition of Tissue Samples

Biological samples, such as blood samples or biopsies, are taken from appropriate anatomic sites or tissues utilizing standard techniques routinely employed in medical clinics and hospitals. For example, a liver tissue sample is obtained from a person to be tested for HBx/8p11-positive HCC using a method of the present invention. Collection of a blood or tissue sample, e.g., a liver tissue sample, from an individual is performed in accordance with the standard protocol hospitals or clinics generally follow, such as during a blood drawing, biopsy, or surgical procedure. An appropriate amount of blood or tissue sample, especially a liver tissue sample taken from a suspected liver tumor site, is collected and may be stored according to standard procedures prior to further preparation.

The analysis of DNA or RNA for the presence of the HBx/8p11 specific polynucleotide sequences (e.g., a DNA sequence comprising the sequence of SEQ ID NO:1 or an mRNA having the sequence set forth in SEQ ID NO:4) found in a patient's biological sample according to the present invention may be performed using, e.g., liver tissue, especially taken from a suspected liver tumor site. The methods for preparing blood or tissue samples for nucleic acid extraction are well known among those of skill in the art. For example, a subject's liver tissue sample should be first treated to disrupt cellular membrane so as to release nucleic acids contained within the cells.

B. Extraction and Quantitation of DNA or RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

Methods for extracting DNA from a biological sample are well known and routinely practiced in the art of molecular biology, see, e.g., Sambrook and Russell, supra. RNA contamination should be eliminated to avoid interference with DNA analysis.

1. PCR-Based Detection of Nucleic Acids

Once DNA or RNA is extracted from a sample, the presence of HBx/8p11 specific polynucleotide sequence (e.g., a sequence comprising SEQ ID NO:1 from HBV fused with a genomic sequence at 8p11, or mRNA having the polynucleotide sequence set forth in SEQ ID NO:4) may be detected and the amount quantified. The preferred method for detecting and/or quantifying the DNA or RNA is an amplification-based method, e.g., by polymerase chain reaction (PCR), especially reverse transcription-polymerase chain reaction (RT-PCR).

While DNA may be directly used in an amplification process, a DNA copy (cDNA) of the target mRNA being analyzed must be synthesized prior to the amplification step. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

In some cases, an amplification-based method can be used as an initial screening step to provide a preliminary indication whether a sequence insertion has taken place at 8p11. For example, a set of two primers, each specifically hybridizing to a portion of SEQ ID NO:2 or a portion of SEQ ID NO:3 (e.g., at least 10, 15, or 20 contiguous nucleotides), may be used in a PCR process to amplify the DNA sequence between the two hybridization sites. If an amplicon is detected in the size that is approximated 297 bp longer than the genomic distance between the two hybridization sites, one can conclude that the subject being tested likely has HBx/8p11-positive HCC or is at risk of developing the disease. Such preliminary testing is particularly useful in patients already have a diagnosis of HCC, and can be readily verified by confirming the presence of SEQ ID NO:1 within the amplicon, for example, by a hybridization assay using a polynucleotide probe that specifically binds SEQ ID NO:1 or its complement.

2. Other Detection Methods

The HBx/8p11 specific DNA or RNA (e.g., a DNA sequence comprising SEQ ID NO:1 from HBV fused with a genomic sequence at 8p11, or an RNA having the polynucleotide sequence set forth in SEQ ID NO:4) can also be detected using other standard techniques, well known to those of skill in the art. Although the detection step is typically preceded by an amplification step, amplification is not required in the methods of the invention. For instance, the DNA or RNA may be identified by size fractionation (e.g., gel electrophoresis), whether or not proceeded by an additional step such as reverse transcription, enzymatic digestion, or amplification. After running a sample in an agarose or polyacrylamide gel and labeling with ethidium bromide according to well-known techniques (see, e.g., Sambrook and Russell, supra), the presence of a band of the same size as the standard comparison is an indication of the presence of a target mRNA, the amount of which may then be compared to the control based on the intensity of the band. Optionally and alternatively, oligonucleotide probes specific to target DNA or RNA can be used to detect the presence of such DNA or RNA species and indicate the amount of such DNA or RNA in comparison to a standard baseline comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

For the purpose of analyzing a genomic sequence at the location of 8p11 for detecting insertion of HBV sequence such as SEQ ID NO:1, in situ hybridization techniques can be used. Typically, there is no need to extract genomic DNA prior to fixing the cells taken from a patient sample (e.g., from liver or a suspected liver tumor) on a solid substrate, e.g., a light transmissible plastic or glass slide, and exposing the fixed cells under appropriate conditions to a polynucleotide probe that is capable of specifically hybridizing with SEQ ID NO:1 or its complement sequence. The probe is often conjugated with a detectable moiety, such as a fluorescent dye, for easy detection of the target sequence.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the DNA or mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255: 137-149, 1983.

VI. Treatment of HBx/8p11-Positive HCC

By illustrating the presence of an mRNA having a HBV-human chromosome 8 fusion polynucleotide sequence such as the one set forth in SEQ ID NO:4 in certain HCC cases, the present invention further provides a means for treating patients suffering from this type of HCC: by way of suppressing the level of such mRNA. As used herein, treatment of HBx/8p11-positive HCC encompasses reducing, lessening, eliminating, or reversing one or more of the symptoms of HCC, as well as preventing or delaying the onset of one or more of the relevant symptoms.

A. Inhibitory Nucleic Acids

Suppression of the HBx/8p11 specific mRNA can be achieved through the use of inhibitory nucleic acids Inhibitory nucleic acids can be single-stranded nucleic acids or oligonucleotides that can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids or oligonucleotides.

In one embodiment, the inhibitory nucleic acid can specifically bind to a target polynucleotide sequence (e.g., an mRNA having the nucleotide sequence set forth in SEQ ID NO:1). Administration of such inhibitory nucleic acids can suppress the level of an HBx/8p11 specific mRNA and eliminate or reduce its effect. Since this target mRNA sequence is disclosed herein as SEQ ID NO:1, one can derive a suitable inhibitory nucleic acid from the sequence, species homologs, and variants of these sequences.

By binding to the target nucleic acid, the inhibitory nucleic acid can inhibit or counter the function of the target nucleic acid. This could, for example, be a result of blocking DNA transcription, processing or poly(A) addition to mRNA, DNA replication, translation, or promoting inhibitory mechanisms of the cells, such as promoting RNA degradation Inhibitory nucleic acid methods therefore encompass a number of different approaches to altering expression of specific genes that operate by different mechanisms. These different types of inhibitory nucleic acid technology are described in Helene and Toulme (1990) *Biochim. Biophys. Acta.*, 1049:99-125.

Inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme, supra.

More commonly, inhibitory nucleic acids are designed to bind to mRNA or mRNA precursors. Inhibitory nucleic acids are used to prevent maturation of pre-mRNA Inhibitory nucleic acids may be designed to interfere with RNA processing, splicing or translation. The inhibitory nucleic acids are often targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory antisense nucleic acid complementary to regions of a target mRNA inhibits protein expression (see, e.g., Wickstrom et al. (1988) *Proc. Nat'l. Acad. Sci. USA* 85:1028-1032 and Harel-Bellan et al. (1988) *Exp. Med.*, 168:2309-2318). As described in Helene and Toulme, supra, inhibitory nucleic acids targeting mRNA have been shown to work by several different mechanisms in order to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme, supra.

The inhibitory nucleic acids can also be used to induce chemical inactivation or cleavage of the target genes or mRNA. Chemical inactivation can occur by the induction of crosslinks between the inhibitory nucleic acid and the target nucleic acid within the cell. Alternatively, irreversible photochemical reactions can be induced in the target nucleic acid by means of a photoactive group attached to the inhibitory nucleic acid. Other chemical modifications of the target nucleic acids induced by appropriately derivatized inhibitory nucleic acids may also be used.

Cleavage, and therefore inactivation, of the target nucleic acids can be effected by attaching to the inhibitory nucleic acid a substituent that can be activated to induce cleavage reactions. The substituent can be one that effects either chemical, photochemical or enzymatic cleavage. For example, one can contact an mRNA:antisense oligonucleotide hybrid with a nuclease which digests mRNA:DNA hybrids. Alternatively cleavage can be induced by the use of ribozymes or catalytic RNA. In this approach, the inhibitory nucleic acids would comprise either naturally occurring RNA (ribozymes) or synthetic nucleic acids with catalytic activity.

Inhibitory nucleic acids can also include RNA aptamers, which are short, synthetic oligonucleotide sequences that bind to proteins (see, e.g., Li et al. (2006) *Nuc. Acids Res.* 34: 6416-24). They are notable for both high affinity and specificity for the targeted molecule, and have the additional advantage of being smaller than antibodies (usually less than 6 kD). RNA aptamers with a desired specificity are generally selected from a combinatorial library, and can be modified to reduce vulnerability to ribonucleases, using methods known in the art.

B. Pharmaceutical Compositions

1. Formulations

Compounds of the present invention (e.g., inhibitory nucleic acids for suppressing HBx/8p11 mRNA having the sequence of SEQ ID NO:4) are useful in the manufacture of a pharmaceutical composition or a medicament comprising an effective amount thereof in conjunction or mixture with excipients or carriers suitable for application. A pharmaceutical composition or medicament can be administered to a subject for the treatment of HBx/8p11-positive HCC.

A preferred pharmaceutical composition for inhibiting HBx/8p11 mRNA comprises (i) an inhibitory oligonucleotide or nucleic acid as described herein and (ii) a pharmaceutically acceptable excipient or carrier. The terms pharmaceutically-acceptable and physiologically-acceptable are used synonymously herein. The inhibitory oligonucleotide or nucleic acid may be provided in a therapeutically effective dose for use in a method for treatment as described herein.

An inhibitory oligonucleotide of the invention can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., hepatocytes), or with other therapeutic or immunogenic compositions. Thus, liposomes filled with a desired inhibitory oligonucleotide can be directed to liver, where the liposomes then deliver the selected inhibitory oligonucleotide. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a nucleic acid for inhibiting HBx/8p11 mRNA, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the inhibitory nucleic acid may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The inhibitors can also be formulated in rectal compositions, for example, suppositories or retention enemas, for example, containing conventional suppository bases, for example, cocoa butter or other glycerides.

Furthermore, the active compounds and agents can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that suppresses/inhibits the level of HBx/8p11 specific mRNA, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control HBx/8p11-positive HCC as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of inhibitory nucleic acid will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat HBx/8p11-positive HCC described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for some of the inhibitory nucleic acids described herein are provided. Dosage for an inhibitory nucleic acid, such as an anti-HCC aptamer, can be between 0.1-0.5 mg/eye, with intravitreous administration (e.g., 5-30 mg/kg). Small organic compounds can be administered orally at between 5-1000 mg, or by intravenous infusion at between 10-500 mg/ml. Monoclonal antibody inhibitors can be administered by intravenous injection or infusion at 50-500 mg/ml (over 120 minutes); 1-500 mg/kg (over 60 minutes); or 1-100 mg/kg (bolus) five times weekly. Peptide inhibitors can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, an inhibitory nucleic acid. The additional therapeutic compound can also be administered separately, in a separate composition, or a different dosage form than the inhibitory nucleic acid. Some doses of the inhibitory nucleic acids of the invention can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess the level of an mRNA indicating an HBV sequence insertion at 8p11 region in a subject, which can be used for various purposes such as detecting or diagnosing the presence of HBx/8p11-positive HCC, determining the risk of developing HCC, and devising a therapeutic or prophylactic regimen in a patient.

Kits for carrying out assays for determining HBx/8p11 specific mRNA level typically include at least one oligonucleotide useful for specific hybridization with a segment of the HBV sequence inserted into human chromosome 8p11 region, or a complementary sequence of the segment. In some cases, the oligonucleotide may hybridize to a sequence comprising a part of the HBV sequence and a part of 8p11 genomic sequence, such as SEQ ID NO:1, SEQ ID NO:4, or its complement. Optionally, this oligonucleotide is labeled with a detectable moiety. In some cases, the kits may include at least two oligonucleotide primers that can be used in the amplification of HBx/8p11 mRNA by PCR, particularly by RT-PCR.

Typically, the kits of this invention may provide instruction manuals to guide users in analyzing test samples and assessing the presence or risk of HBx/8p11-positive HCC in a test subject.

In a further aspect, the present invention can also be embodied in a device or in a system comprising one or more such devices, which is capable of carrying out all or some of the method steps described herein. For instance, in some cases, the device or system performs the following steps upon receiving a biological sample (e.g., a liver or liver tumor tissue sample) taken from a subject being tested for detecting HBx/8p11-positive HCC, assessing the risk of developing HCC, or devising treatment plan of the condition: (a) determining in the sample the presence or amount/concentration of a polynucleotide that indicate an insertion of HBV sequence into 8p11 region (e.g., an mRNA that comprises SEQ ID NO:4); and (b) providing an output indicating whether HBx/8p11-positive HCC is present in the subject or whether the subject is at risk of developing HCC, or whether there is a need for therapeutic or prophylactic treatment of the subject's HBx/8p11-positive HCC. In other cases, the device or system of the invention performs the task of step (b) after step (a) has been performed and the information obtained from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Chronic hepatitis B (HBV) infection is a strong predisposing factor in the development of human hepatocellular carcinoma (HCC). Despite viral integration can be detected in >85% of tumors, the insertional mutagenesis that underlie HCC development remains largely unclear. The present inventor reports for the first time on the identification of a novel viral-human transcript that is non-protein coding but holds functional significance in the liver oncogenesis. By RS-PCR screening for HBV integrants and RACE cloning, a chimeric transcript was identified as comprising sequences from HBx and chr.8p11 intergenic region, with a micro-homology sequence of GTG shared at the flanking juncture. Recurrent presence of this transcript can be found in 24.4% of HBV-related HCC tumors (n=90), where a prognostic indication of shorter patient survival is shown. Knockdown of HBx/8p11 resulted in marked inhibition on cell motility and invasion with increased E-Cadherin and γ-catenin expressions, and down-regulation of fibronectin, indicating its likely contribution in the Epithelial-to-Mesenchymal Transition (EMT) phenotype. A corresponding diminution of β-catenin nuclear localization and reduced β-catenin transactivating activity were also found, which enforced a role for HBx/8p11 in the membrane-bound E-Cadherin/β-catenin complex. Transfection of HBx/8p11 in immortalized hepatocyte L02 promoted colony growth, although this effect was not apparent in expressing vectors with either HBV components or flanking 8p11 sequence. Over-expression of HBx/8p11 in L02 also induced cell invasiveness and migration via promoting EMT. It was further demonstrated in liver-specific transgenic model that mice with HBx/8p11 transgene were more susceptible to DEN-induced tumor formation than wild-type. These data highlight importance for the HBx/8p11 ncRNA transcript in conferring oncogenic advantages and may represent an elemental predisposing factor in the initiation and progression of HCC.

INTRODUCTION

Epidemiological studies have clearly demonstrated a strong association between chronic infection with HBV and the development of hepatocellular carcinoma (HCC) (McMahon, *Hepatology*. 2009; 49(5):S45-55; Beasley, *Cancer*. 1988; 61(10):1942-56). Chronic carriers of HBV are believed to have a 5-15 folds increased risk of developing HCC compared to non-carriers (El-Serag and Rudolph, *Gastroenterology*. 2007; 132(7):2557-76). Several direct and indirect mechanisms on the viral induction towards HCC development have hence been proposed. Long lasting viral multiplications and expression of HBV proteins are known to stimulate the host immune response, leading to liver inflammation, cirrhosis and ultimately cancer (Chisari and Ferrari, *Annu Rev Immunol*. 1995; 13:29-60). On the other hand, a more direct oncogenic effect of HBV integrations on the hepatic carcinogenesis has also been proposed based on the fact that over 85-90% of HBV-related HCC tumors harbor one or more sites of HBV insertion, and they usually precede the development of HCC (Buendia, *Adv Cancer Res*. 1992; 59:167-226; Bréchot et al., *Semin Cancer Biol*. 2000; 10(3):211-31). The majority of HCC tissue also exhibits clonal expansion of tumoral cells carrying the same integration site (Gozuacik et al., *Oncogene*. 2001; 20(43):6233-40). Implication of viral integrants in the development of HCC has thus been long suggested, although details on the induced carcinogenetic changes remain elusive.

Earlier reports using low-resolution approaches of Southern blotting and cloning strategies suggested HBV integrations to occur randomly throughout the whole genome, leading to the presumption that there are no preferential sites of insertion (Matsubara and Tokino, *Mol Biol Med*. 1990; 7(3): 243-60). More recent high-resolution analysis revealed many HBV integrants occur within or near chromosome fragile sites, or in the proximity of important cancer-related genes that have been postulated to prone genetic instability (Kremsdorf et al., *Oncogene*. 2006; 25(27):3823-33). Recent analysis further highlights preferential integrations in the cellular genome at sites that harbor genes involved in regulating cell signaling, proliferation and viability (Murakami et al., *Gut*. 2005; 54(8):1162-8). Attempts have been made to deconvolute the HBV DNA junctures in primary HCC tumors and cell lines using restriction-site PCR (RS-PCR) screening (Thorland et al., *Oncogene*. 2003; 22(8):1225-37). The detection of recurring 8p11 insertional site of exact viral-human sequences prompted further cloning for the full-length transcript. Using both 5' and 3' RACE, a novel viral-human chimeric sequence of 674 bp was isolated and found to be transcribed from the site of insertion. The fusion transcript encompassing part of the HBx open reading frame (297 bp) and intergenic sequence from 8p11 (380 bp) shared a 3 bp micro-homology (GTG) between the viral and human sequences. Examination of HBV/8p11 chimeric sequence in HCC tumors and cell lines indicated a remarkable occurrence of ~25%, signifying this integration is a non-random event. Functional characterization of HBx/8p11 demonstrated its role in promoting metastatic potentials of HCC cells through regulating the Epithelial-Mesenchymal Transition (EMT) phenotype. More interestingly, it was found that HBx/8p11 exerts it oncogenic effects as a long non-coding RNA (ncRNA), which is usually defined at a size of greater than 200 bp (Hung and Chang, *RNA Biol.* 2010; 7(5):582-5).

Recent genome-wide studies have begun to highlight abundant non-protein-coding RNAs (ncRNAs), including miRNAs, siRNA and various classes of long ncRNAs, transcribed in the mammalian genome. There is also increasing evidence revealing vital roles for ncRNA in regulating cellular processes as well as their aberrant expressions in contributing to disease phenotypes. However other than miRNAs, only a handful of long ncRNAs have been studied in the hepatocarcinogenesis (Matouk et al., *PLoS One.* 2007; 2(9):e845; Matouk et al., *Eur J Gastroenterol Hepatol.* 2009; 21(6):688-92; Oliva et al., *Exp Mol Pathol.* 2009; 87(1):12-9; Panzitt et al., *Gastroenterology.* 2007; 132(1):330-42). This study on HBV-related insertional mutagenesis has allowed isolation of previously undescribed viral-human chimeric ncRNA that confers advantages in tumor growth and mediator of cell motility, and, more importantly, a proven role in the liver pathogenesis.

Materials and Methods

Restriction-Site PCR (RS-PCR).

Genomic DNA extracted from 16 HBV infected HCC tumors and 10 cell lines (Hep3B, HKCI-3, -4, -7, -9, and SNU 387, 398, 423, 449, 475) (Pang et al., *Genes Chromosomes Cancer.* 2002; 33(2):150-9; Chan et al., *Mod Pathol.* 2006; 19(12):1546-54) were subjected to RS-PCR according to method previously described (Thorland et al., *Oncogene.* 2003; 22(8):1225-37). Common fragile sites are preferential targets for HPV16 integrations in cervical tumors (Ferber et al., *Oncogene.* 2003; 22(24):3813-20). The technique of RS-PCR allows amplification of unknown sequence that lies adjacent to known sequence (Sarkar et al., *PCR Methods Appl.* 1993; 2(4):318-22). In this study, to retrieve unknown cellular sequence adjoining to HBV insertion, PCR was performed with primers for known HBV ORFs and individual RSO primers that recognize a given restriction enzyme recognition site. Specific HBV-primers designed based on the conserved regions of prevailing genotypes B and C were used in hemi-nested PCR analysis along with unique RSO primers. First round RS-PCR was performed using 100 ng of DNA in thermal cycling condition of 94° C. for 30 sec, 45° C. for 30 sec, and 68° C. for 3 min+20 sec per cycle at for 25 cycles and final extension for 10 min at 72° C. In second round PCR, 2 µl of the first round PCR product was subjected to the same thermal cycling condition as first round, except the annealing temperature was raised to 55° C. Prominent bands shown from agarose gel electrophoresis were excised and extracted for DNA before subjected to direct sequencing on ABI 3100 Genetic Analyser (Applied Biosystems, USA) to determine the flanking sites. Sequence homology searches were conducted using BLASTN algorithms on the HBV genome assembly and the human sequences adjunct to viral insertion.

Rapid Amplification of cDNA Ends (RACE).

Trizol extracted total RNA from HKCI-4 was subjected to 5' and 3' RACE to isolate the full length HBx/8p11 transcript (BD SMART™ RACE cDNA Amplification, BD Biosciences). For 3'-RACE, cDNA synthesized from SuperScript™ II reverse transcription (Invitrogen) was amplified by HBV specific primer 5'-TGCTGCCAACTGGATCCT-GCG-3' (SEQ ID NO:9) and universal primer using thermal cycling condition of 94° C. for 30 sec, 68° C. for 30 sec and 72° C. for 3 min by 25 cycles. A nested PCR was performed using similar cycle conditions as the first round, except for nested HBV-specific primer 5'-ACGTCCTTTGTT-TACGTCCCGTC-3' (SEQ ID NO:10) and nested universal primer being used. For 5'-RACE, reverse transcribed cDNA was subjected to thermal cycling condition of 94° C. for 30 sec, 68° C. for 30 sec and 72° C. for 3 min by 25 cycles using human-specific primer 5'-TGCTGCCAACTGGATCCT-GCG-3' (SEQ ID NO:11) and universal primer. A second nested PCR was performed using a human-specific primer 5'-ATTCCTACCAAGAGCAGGCA-3' (SEQ ID NO:12) and nested universal primer. The PCR product obtained was subjected to agarose gel electrophoresis, and all visible bands were excised from gel and purified for DNA. BigDye Terminator Cycle Sequencing (Applied Biosystems) was performed on TOPO TA (Invitrogen) cloned gel purified products. Alignment of sequence was support by BLASTN in defining the sequences derived from HBV and the human 8p11 region.

HBx/8p11 Expression in HCC.

Tumorous liver tissues were collected from 90 patients who underwent curative surgery for HCC at the Prince of Wales Hospital in Hong Kong. Informed consent was obtained from each patients recruited, and the study protocol was approved by the Clinical Research Ethics Committee of the Chinese University of Hong Kong. A diagnosis of HCC was confirmed from histology examination. Patients recruited were all chronic carriers of HBV (100%), and so were the 10 HCC cell lines studied. HBx/8p11 expression in HCC tumors and cell lines was analyzed by RT-PCR. Total RNA was converted to cDNA using SuperScript™ II reverse transcriptase (Invitrogen) and amplified in a hemi-nested PCR using specific primers designed at juxtapose positions of the viral-human flanking junction. For the first round of PCR, primers 5'-GGACTCTACCGTCCCCTTCT-3' (SEQ ID NO:13) and 5'-AGTAGGGGACTGCTGGATCA-3' (SEQ ID NO:14) were used with the thermal cycling condition as follows: 95° C. for 30 sec, 58° C. for 30 sec and 72° C. for 30 sec for 30 cycles. The second round of PCR was performed using primers 5'-CCGTCTGTGCCTTCTCATCT-3' (SEQ ID NO:15) and 5'-AGTAGGGGACTGCTGGATCA-3' (SEQ ID NO:16) and 30 cycles of thermal cycling condition of 95° C. for 30 sec, 60° C. for 30 sec and 72° C. for 30 sec.

RNA Interference (RNAi) Knockdown of HBx/8p11.

Oligonucleotide targeting the flanking junction of the viral-human HBx/8p11 transcript (289-313 bp) was designed: siHBx/8p11, 5'-ACCACCGUGUUGUUGAG-GAUGUGAA-3' (SEQ ID NO:5). HKCI-4 cultured in AIM-V (Invitrogen) supplemented with 10% fetal bovine serum and 1% L-glutamine was transfected with siHBx/8p11 using Lipofectamine 2000 (Invitrogen). The efficacy of transcript knockdown was conformed and monitored by RT-PCR. The effect of knockdown on cell viability was examined by the MTT assay.

Expression Vector Constructions and Transfection.

A number of plasmids were constructed based on the complete sequence obtained on HBx/8p11. These included a full-length HBx/8p11$^{1-674}$, variants HBx$^{1-297}$ and 8p11$^{295-674}$ each of which constituted the viral and human component and the GTG microhomology, and HBx/8p11$^{1-312}$* that contained the HBx fragment and partial sequence of 8p11 prior to a stop codon. Detail cloning map shown in FIG. 6. Each plasmid was cloned into a pEGFP-C2 expression vector (Clontech) with a GFP sequence tag to examine the GFP-fused protein translation. The series of plasmids was also cloned into another derivative, pEGFP-C2R(−), with a deleted EGFP coding sequence for use in transfection assays. Cloned plasmids in pEGFP-C2 and pEGFP-C2R(−) were sequence verified and their expressions confirmed by RT-PCR in transfected cells. Expression vectors were transfected into the immortalized hepatocyte cell line L02 using Lipofectamine 2000 (Invitrogen).

Matrigel Invasion and Cell Migration Assays.

Cell migration was assessed by 24-well Costar Transwell (Corning) and cell invasion by 24-well BioCoat Matrigel Invasion Chambers (BD Biosciences) according to previously described (Pang et al., *Hepatology*. 2007; 46(2):436-45). For Transwell migration, transfected HKCI-4 and L02 cells at $2 \times 10^4$ were seeded, whereas $2 \times 10^4$ HKCI-4 and $5 \times 10^4$ L02 transfected cells were seeded for Matrigel invasion assay. The number of cells invaded/migrated to the underside of the membrane was scored from >20 microscopic fields (400×) and the mean value was expressed as a percentage relative to mock or vector control.

Colony Formation Assay.

L02 transfected with the plasmid constructs HBx/8p11$^{1-674}$, HBx$^{1-297}$, 8p11$^{295-674}$, HBx/8p11$^{1-312}$* and vector were seeded at a density of $2 \times 10^4$ cells/well in 6-well culture plate. Cells were selected in 0.5 mg/ml of G418 for 21 days, and the colonies developed were stained with crystal violet. Visible colonies containing >50 cells were scored, and compared between different plasmid transfections.

Western Blotting.

Twenty micrograms of protein were separated by 8-12% SDS-PAGE and transferred electrophoretically onto PVDF membrane. Blots were incubated with antibodies against E-cadherin, γ-catenin, TCF3, c-Myc (Cell Signaling), fibronectin (Sigma), β-catenin (BD Biosciences), active β-catenin (Millipore), c-Myc (Santa Cruz Biotechnology), ZEB1 (Abcam) or GAPDH (Chemicon). Secondary antibody conjugated to horseradish peroxidase was used, and protein bands were visualized using enhanced chemiluminescence detection (GE Healthcare).

TOP/FOPflash Luciferase Reporter Assay.

TCF-dependent luciferase activity in HKCI-4 and L02 cells following siHBx/8p11 treatment or full-length HBx/8p11$^{1-674}$ ectopic expression were measured. Fifty micrograms of pTOPflash or pFOPflash with 20 μg of Renilla plasmid were co-transfected. The activities of firefly and Renilla luciferases were detected using Dual-Luciferase® Reporter Assay System (Promega). Relative luciferase activities were calculated by normalizing the ratios of TOP/FOP with the Renilla luciferase activities.

Immunofluorescence Microscopy.

After fixation with 4% paraformaldehyde in PBS, cells grown on coverslip were permeabilized by 0.5% Triton X-100 and incubated with primary antibody (E-cadherin, γ-catenin, fibronectin or active β-catenin, 1:100 dilution) overnight at 4° C. After PBS washes, cells were incubated with FITC-conjugated goat anti-mouse or goat anti-rabbit IgG (1:250, Invitrogen). Counterstained in DAPI, cells were examined under a laser confocal microscope (LSM5 PASCAL, Carl Zeiss).

Liver-Specific Transgenic Model.

Full-length HBx/8p11 was cloned into expression vector containing a liver-specific transthyretin (TTR) promoter to generate a HBx/8p11 transgene. Full-length HBx/8p11 was amplified using the forward and reverse primer containing NruI restriction site. Transgenic mice were made following the standard protocol outlined in references (Hogan et al., *Manipulating the mouse embryo: a laboratory manual*. New York, Cold Spring Harbour Laboratory Press. 1986; Pinkert Calif. *Transgenic animal technology—A laboratory handbook*. San Diego, Academic Press, Inc. 1994). PCR on tail DNA was employed to screen for positive HBx/8p11 transgenic mice. Mice of age 15 days received a single intraperitoneal injection of DEN (5 mg/kg body weight; Sigma). After 8 months, mice were sacrificed and liver RNA was extracted to confirm HBx/8p11 expression. The presence of surface nodules in HBx/8p11 and wild type transgenic mice were evaluated and compared. The development of HCC was confirmed histologically by an experienced pathologist. All experiments were conducted in accordance with guidelines by the Animal Experimentation Ethics Committee of the Chinese University of Hong Kong.

Statistics.

Data are presented as mean±S.E.M, unless otherwise indicated. Kaplan-Meier plots and log-rank tests were used for survival analysis. The independent Student's t test was used to compare the cell motility between groups. A P value less than 0.05 was considered statistically significant.

Results

Mapping of HBV Integration Sites and Flanking Human Sequences

High-throughput PCR-based RS-PCR has previously facilitated direct identifications of adjoining human sequences at sites of papillomavirus integration (19). RS-PCR was utilized to screen 16 HCC tumors and 10 cell lines for HBV integrants. A total of 34 flanking cellular sequences were isolated from 22 cases that displayed one or more integration sites. Many of the viral integration sites were found to occur in the human intergenic regions that contain at least a portion of a repetitive element (SINE and LINE) in the human-flanking sequence. Of the 15 junction fragments that interrupted a known gene, 12 were found in the intronic region of genes, including EFR3B, UPF3A, METAP1, CDH11, TMEM117, AGFG2, ABCC12, GDNF, MLL4, SLC4A1, ITPR2, LOC728323 and CADPS2. Only 3 insertions were determined within an exon (KCNQ4, PCK2 and FN1).

Of particular interest was the finding of a recurring HBV integration that displayed the exact viral human flanking sequence. In primary tumor H210T and cell line HKCI-4, HBV enhancer I and HBx promoter sequences (HKCI-4: 1167-1622; H210T: 1493-1622) were found to insertion at the precise position on chr.8p11.21, which is a LINE1 region (chr.8: 41,613,080-41,613,201) (FIG. 1). In both cases, the 3'-end of integrated HBx sequence shared a common microhomology GTG with the 5'-end of chr.8p11 region (FIG. 1).

Cloning of Full-Length HBx/8p11 and Expression in HCC

Figure 2:
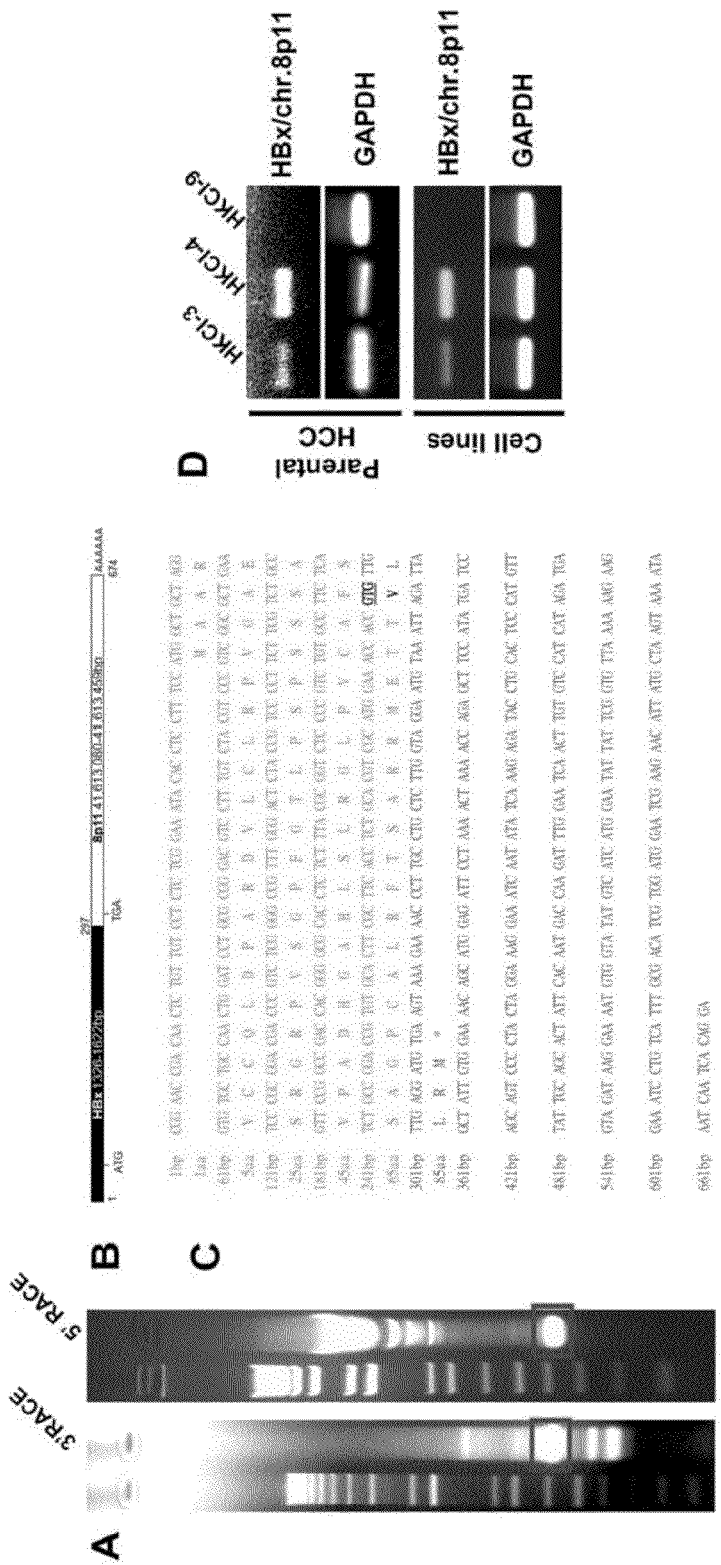
FIG. 2: Identification of HBx/8p11 fusion transcript expression. (A) Agarose gel electrophoresis of RACE PCR product. Red box indicated the HBx/8p11 3'-end (left) and 5'-end (right) PCR products. (B) Schematic organization of full-length HBx/8p11 fusion transcript (SEQ ID NOS:4 and 8). (C) Protein translation of HBx/8p11 fusion transcript. (D) HBx/8p11 RT-PCR analysis on HKCI-3, -4 and -9 cell lines and their parental primary HCC. HKCI-9 is the negative control.

The effect of viral integration on the transcription of HBx and 8p11 sequences was then examined. By 5' and 3' RACE cloning in HKCI-4, a 3'-end transcript of 8p11 was isolated that contained a polyadenylation signal AATAAA and poly (A) tail (FIG. 2A, left panel), and a 5'-end transcript entailing the HBx sequence (FIG. 2A, right panel). Moreover, the juncture sequence that flanked the HBx and chr.8p11 was identical to the RS-PCR sequence obtained. Combining the results obtained from the 3' and 5'-end RACE, a full-length HBx/8p11 fusion transcript of 674 bp was achieved (FIG. 2B). The transcript comprised of 297 bp from HBx, ranged from 1326-1622 bp of HBV genome (accession no.: NC_003977), and 380 bp of chr.8p11 that ranged from 41,613,080-41,613,459 bp; the overlapping 3 bp GTG homology was also maintained in the transcribed sequence (FIG. 2C).

Figure 3A:
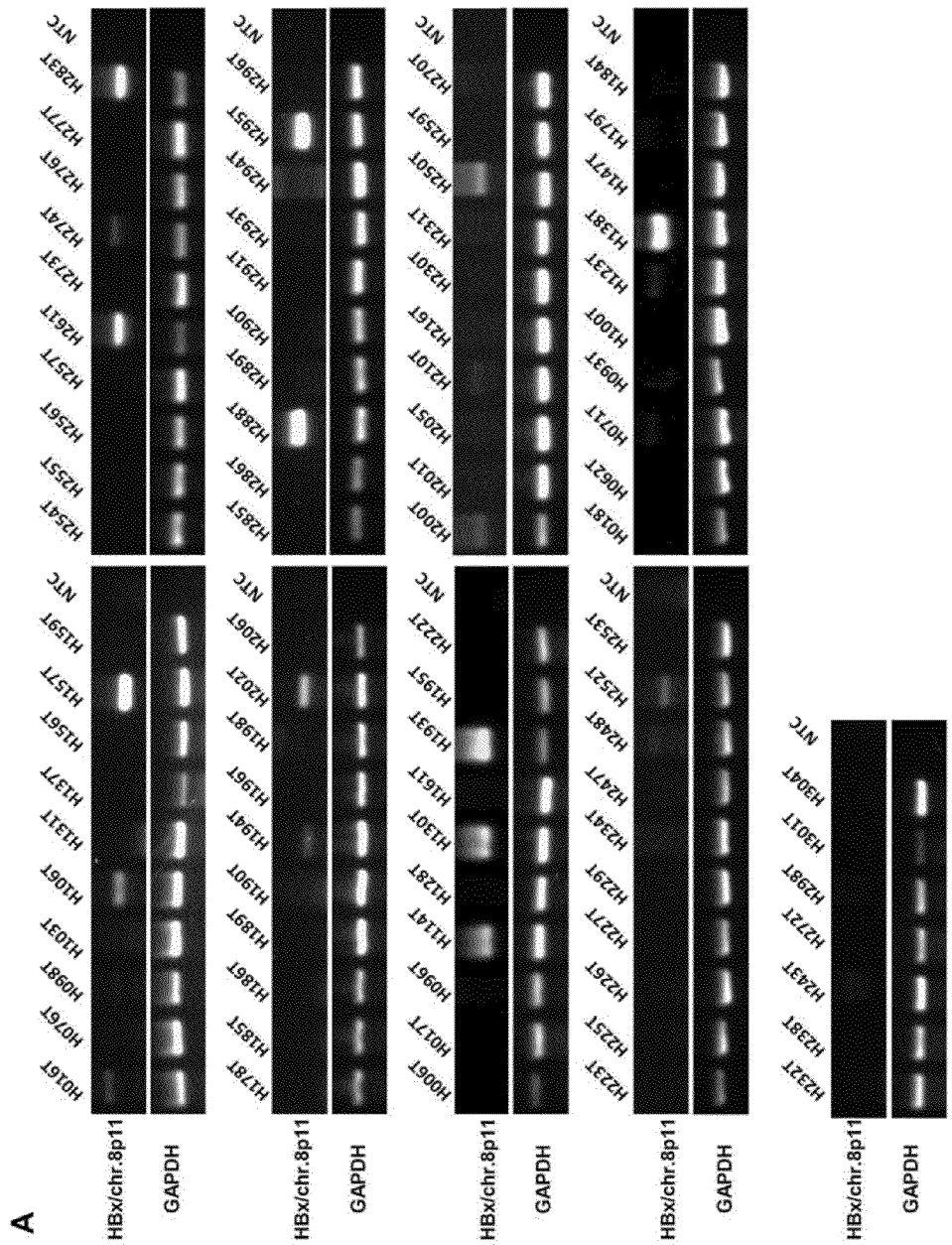
FIG. 3: Expression of HBx/8p11 fusion transcript in HCC. (A) RT-PCR analysis of HBx/8p11 in primary HCC. (B) HCC patients with HBx/8p11 expression (solid; n=21) correlate with a shorter overall survival compared to patients without HBx/8p11 expression (dotted line; n=69).

Recognizing that RS-PCR may have limitations in selecting prominent gel bands for sequencing, the inventor re-examined the expression of HBx/8p11 transcript in HCC cell lines previously subjected RS-PCR analysis. Results obtained from RT-PCR confirmed HBx/8p11 expression in HKCI-4; in addition HKCI-3 and SNU 387 were also shown to be positive for the presence of this transcript (FIGS. 2D and 3A). To rule out the possibility that HBx/8p11 insertion was introduced as a result of prolonged in-vitro culture, the parental tumor of 2 cell lines HKCI-3 and HKCI-4, which have established from in-house, was examined for the same integration site. Cell lines HKCI-3 and HKCI-4 and their parental HCC tumors showed consistent presence of this fusion transcript, while HKCI-9 served as a negative control (FIG. 2D).

Figure 3B:
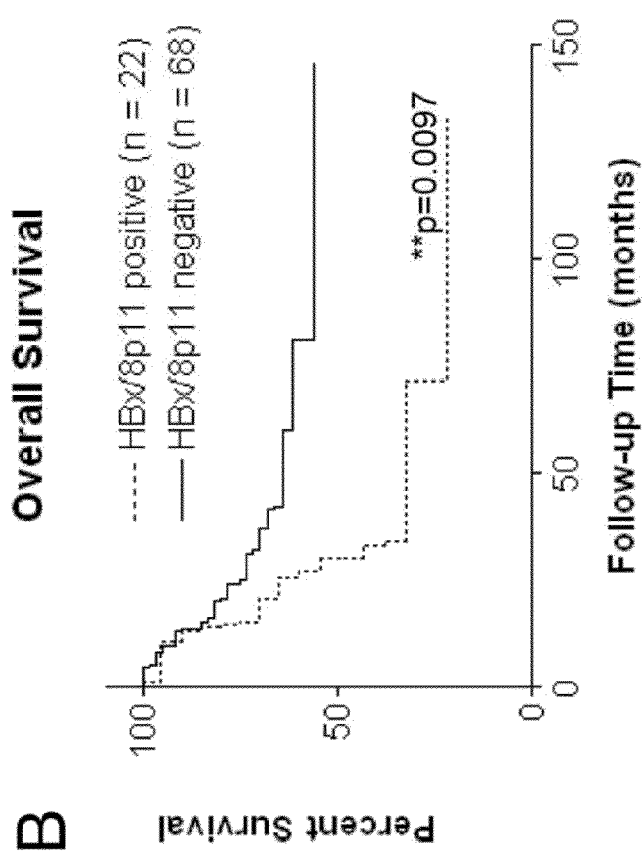

Encouraged by findings from cell lines, the incidence of HBx/8p11 chimeric transcript was further examined in a cohort of 90 HBV-related HCC tumors. RT-PCR analysis indicated common HBx/8p11 expression in 22 of 90 (24.4%) of tumors (FIG. 3B). To affirm the presence of HBx/8p11, all PCR products in primary HCC tumors and cell lines were also sequence verified. The inventor extended the study to investigate the correlation between HBx/8p11 expression and the prognosis of patient. Kaplan-Meier analysis indicated the expression of HBx/8p11 could predict a shorter overall survival of HCC patients (P=0.0097, log-rank test; hazard ratio, 2.331; 95% confidence interval, 1.292-6.398; FIG. 3C).

Figure 4E:
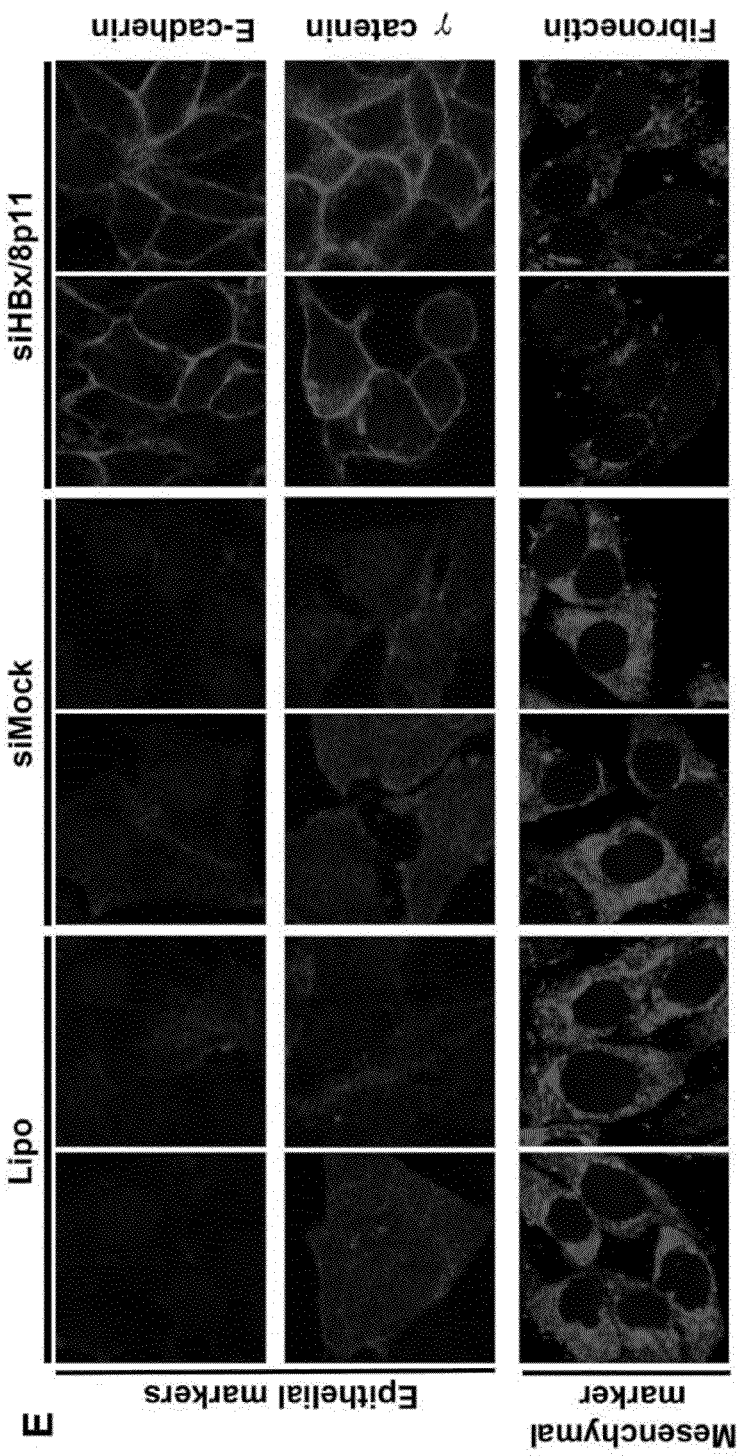
FIG. 4: Knockdown of HBx/8p11 inhibits cell migration and invasion through repression of EMT. Percentage of lipofectamine-treated, siMock-treated and HBx/8p11 knockdown HKCI-4 passed through the transwells in (A) migration assay and (B) Matrigel invasion assay. (C) Expression of epithelial markers (E-cadherin and γ-catenin) and mesenchymal marker (fibronectin), compared between lipofectamine-treated, siMock control and HBx/8p11 knockdown in HKCI-4 by Western blot. HBx/8p11 knockdown was confirmed by RT-PCR. (D) Densitometry of epithelial and mesenchymal markers. (E) immunofluorescence staining of epithelial markers E-cadherin and γ-catenin; mesenchymal marker fibronectin; nuclei were counterstained with DAPI.

Knockdown of HBx/8p11 Inhibits Cell Motility and Invasion Through Repression of EMT It was postulated that the high prevalence of HBx/8p11 expression in HCC may hold biological relevance. To elucidate the potential functional contributions from this fusion transcript, knockdown experiments of HBx/8p11 in HKCI-4 were performed. While siRNA mediated targeting of HBx/8p11 did not seem to affect the cell viability as indicated from MTT assay, more apparent effects were indicated from Transwell migration and Matrigel invasion assays. Knockdown of HBx/8p11 significantly reduced the cell migratory (P=0.040, Student's t test) (FIG. 4A) and invasiveness properties (P=0.040, Student's t test) of HCC cells (FIG. 4B) when compared to siMock control. As EMT is a major molecular mechanism by which cancer cells acquire motile ability to invade the tumor microenvironment, the inventor further investigated the effect of HBx/8p11 expression on the modulation of EMT. Western blotting of siHBx/8p11 treated HKCI-4 revealed increase expression of cohesive epithelial markers E-cadherin and γ-catenin, and a corresponding diminution of mesenchymal specific protein fibronectin (FIGS. 4C and 4D). These findings were further substantiated in immunofluorescence analysis, which corroborated the augmented expression of epithelial E-cadherin and γ-catenin, and their prominent accumulation at the cell membrane when compared to the more diffused cytoplasmic localization of these markers in both lipofectamine-treated and siMock control (FIG. 4E). A decrease in the level of cytoplasmic fibronectin was also observed in siHBx/8p11 treated cells.

Figure 5C:
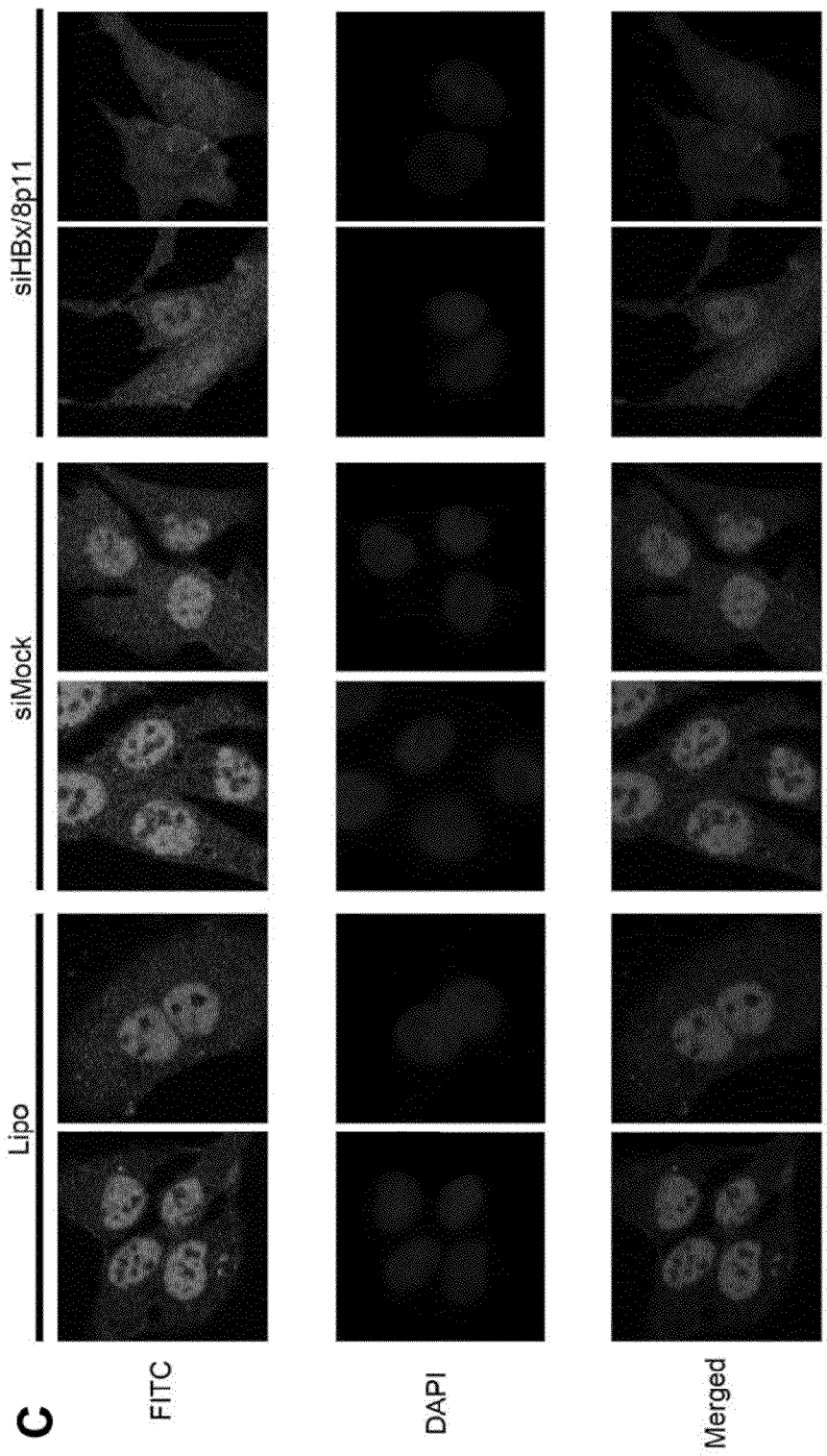
FIG. 5: HBx/8p11 targets Wnt signaling pathway. (A) Western blot analysis showed downregulation of active β-catenin and its target gene cyclin-D1 and c-Myc after HBx/8p11 knockdown. (B) TOP/FOPflash luciferase reporter assay revealed the reduction of β-catenin activity in HBx/8p11 knockdown cells. (C) immunofluorescence staining of active β-catenin. Nuclei were counterstained by DAPI.

It is known that β-catenin forms a membranous complex with the cell adhesion protein E-Cadherin and other catenin proteins. During the process of EMT, β-catenin is dissociated from the membrane-associated E-Cadherin complex and translocates to the nucleus where it coactivates transcription of target genes through the formation of transcriptional complex with TCF/LEF (Nusse, Cell Res. 2005; 15(1):28-32). To examine the plausible effect of HBx/8p11 on the β-catenin signaling, the inventor next examined the nuclear localization and transactivity of β-catenin under the influence of HBx/8p11. In HKCI-4 cells treated with siHBx/8p11, an effect on the total cellular β-catenin protein was not suggested, although marked reduction in the level of active β-catenin was readily shown from Western blot (FIG. 5A). β-catenin target genes cyclin-D1 and c-Myc were also found to display a concordant downregulation in the presence of HBx/8p11 siRNA (FIG. 5A). By TOP/FOPflash luciferase reporter assay, a consistent reduction was found in the transactivation activity of β-catenin following HBx/8p11 knockdown, which is in line with the reduced active β-catenin protein determined (P=0.0076, Student's t test) (FIG. 5B). Cellular distribution of β-catenin as revealed from immunofluorescence staining indicated much reduced nuclear localization of active β-catenin from the effect of siHBx/8p11, whereas lipofectamine-treated and siMock control cells showed more intense accumulation of β-catenin within the nucleus (FIG. 5C).

HBx/8p11 Exerts Functional Effects as ncRNA

Figure 6E:
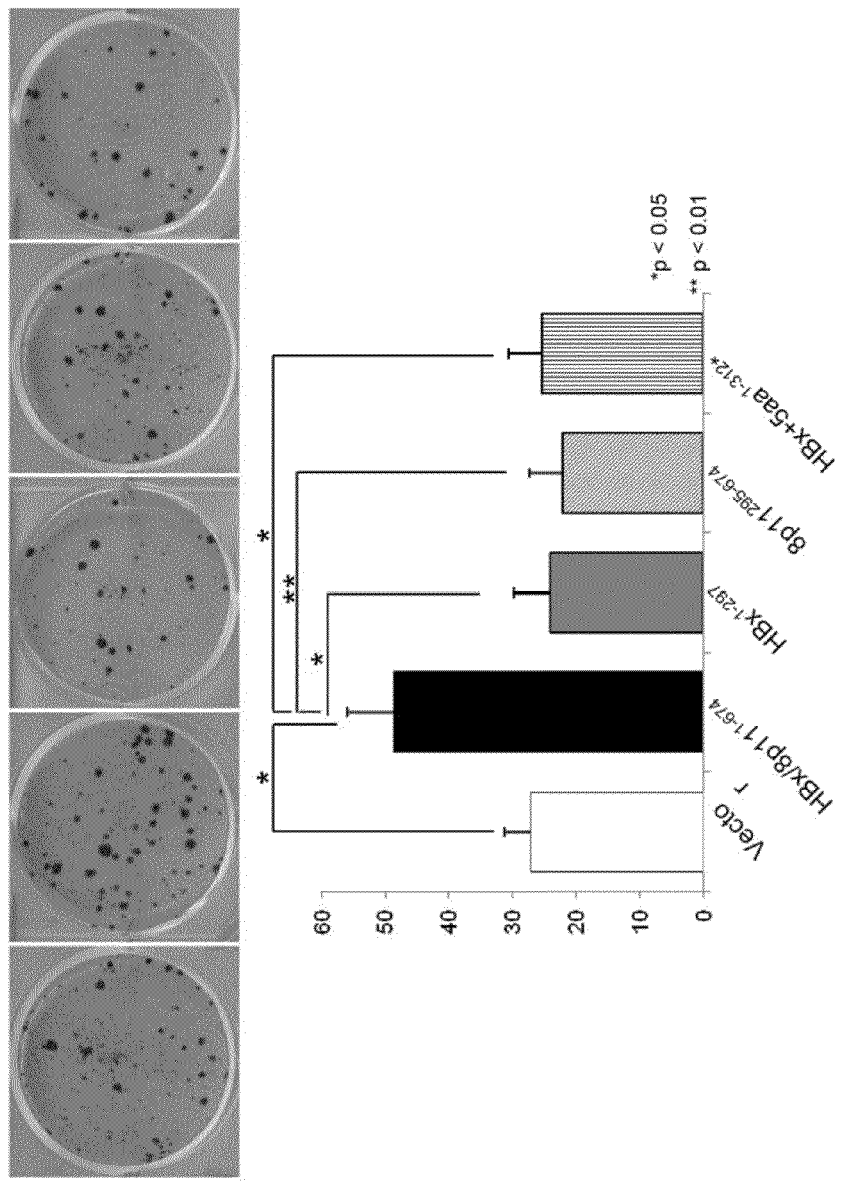
FIG. 6: Overexpression of full-length HBx/8p11 induces cell motility through EMT. (A) Expression constructs of GFP conjugated full-length HBx/8p11$^{1-674}$, HBx$^{1-295}$, 8p11$^{295-674}$ and HBx+5aa$^{1-312}$* containing start (▲) and stop (Δ) codon. (B) GFP conjugated protein expression of full-length HBx/8p11$^{1-674}$, HBx$^{1-295}$, 8p11$^{295-674}$ and HBx+5aa$^{1-312}$* revealed by Western blotting probed against anti-GFP antibody. Cell motility of full-length HBx/8p11$^{1-674}$, expressing cells were compared with HBx$^{1-295}$, 8p11$^z$ and HBx+5aa$^{1-312}$* expressing cells using (C) migration and (D) Matrigel invasion assay. (E) Colony formation assay demonstrated the induced cell proliferation by full-length HBx/8p11 after 21 days of G418 selection. (F) Western blot analysis showed only the full-length HBx/8p11$^{1-674}$ expressing cells induced EMT by downregulation of epithelial marker CK18 and upregulation of mesenchymal markers N-cadherin and vimentin, compared with vector, HBx, 8p11 and HBx+5aa expressing cells. (G) TOP/FOPflash luciferase reporter assay demonstrated the increase in β-catenin activity in full-length HBx/8p11$^{1-674}$ expressing cells.
Figure 7:
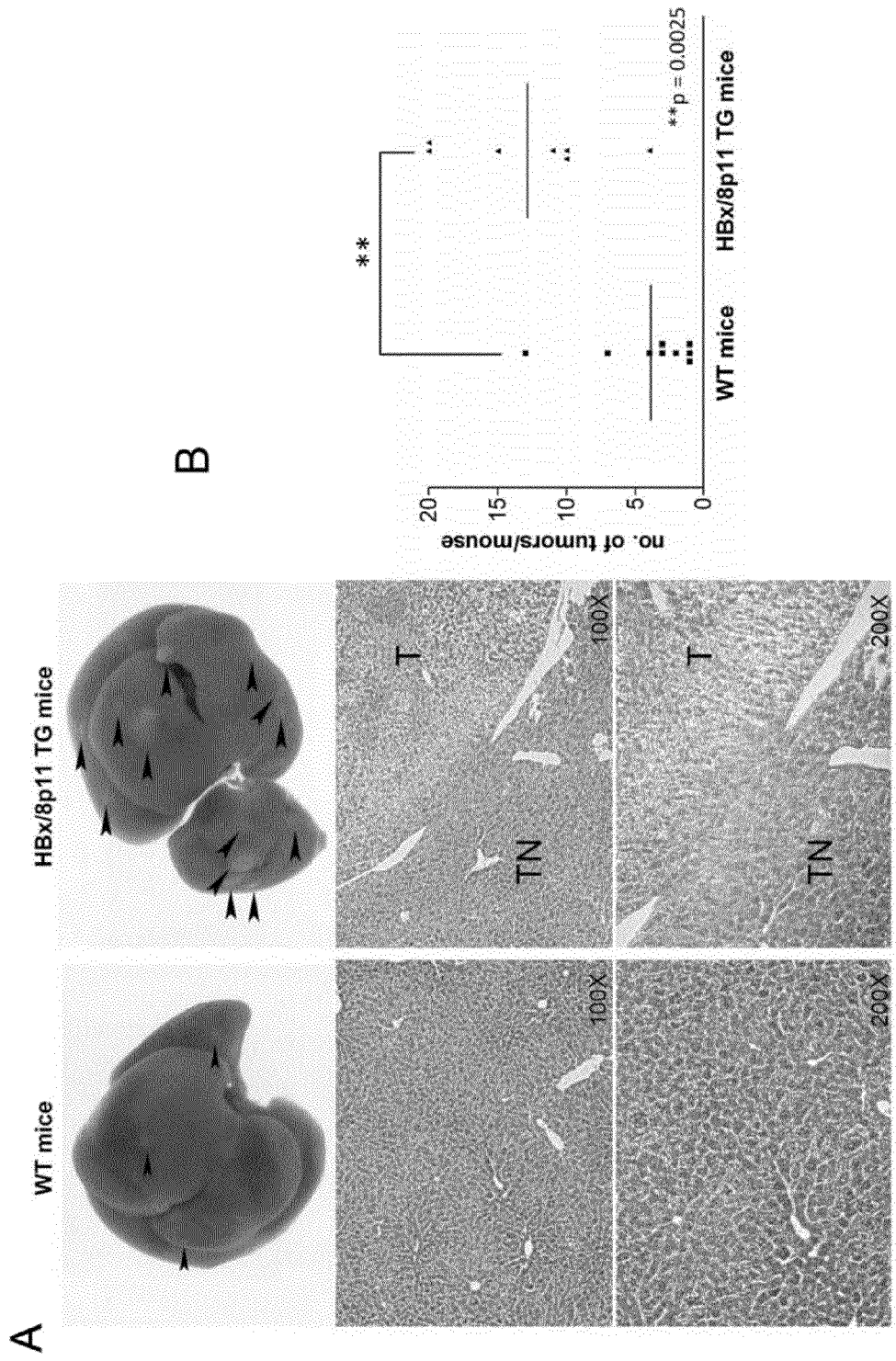
FIG. 7: HBx/8p11 expression increases susceptibility to DEN-induced hepatocarcinogenesis. (A) Typical gross morphology of liver tumors from DEN-treated HBx/8p11 TG mice (right) or wild-type (left) male mice at 8 months. Representative microscopic features of HCC in hematoxylin and eosin (H&E)-stained liver sections of mice. Arrows indicate microscopic HCC. (B) The number of HCCs per mouse was counted and expressed as mean.

To determine whether viral components, human sequence or the full-length HBx/8p11 underlie the functional effects observed, HBx/8p11$^{1-674}$, HBx$^{1-297}$, 8p11$^{295-674}$, HBx/8p11$^{1-312}$* were cloned and expressed for translated protein, and examined as well the functional roles of these expressing vectors in immortalize human hepatocyte cell line L02. The GFP-fused protein expressed from these clones showed protein sizes in accordance to prediction, where minimal differences could be identified between proteins translated from HBx/8p11$^{1-674}$, HBx$^{1-297}$ and HBx/8p11$^{1-312}$* (FIG. 6B). Protein translated from full-length HBx/8p11$^{1-674}$ and HBx/8p11$^{1-312}$* revealed translation of 87 amino acids at 9.57 kDa, both including 5 amino acids contributed from the chr.8p11 sequence prior to a stop codon, whereas the flanking viral HBx$^{1-297}$ and human 8p11$^{295-674}$ components expressed proteins at 9.13 kDa and 0.55 kDa, respectively (FIG. 2C). In functional investigations, however, only L02 cells expressing the full-length HBx/8p11$^{1-674}$ presented prominent in-vitro advantages, including augmentation of colony forming growth (P=0.021) and promotion of cell invasion (P=0.005) and migration (P=0.028) (FIG. 6C-E). Overexpressing HBx$^{1-297}$, HBx/8p11$^{1-312}$* and 8p11$^{295-674}$ in L02, on the other hand, showed similar functional behaviors as vector control. Western blot analysis indicated downregulation of epithelial marker CK18 and upregulation of mesenchymal protein N-cadherin and vimentin in cells expressing HBx/8p11$^{1-674}$ compared to HBx$^{1-297}$, HBx/8p11$^{1-312}$* and 8p11$^{295-674b}$ treated cells (FIG. 6F). This indicated the likely involvement of EMT in L02 cells expressing HBx/8p11$^{1-674}$. Moreover, TOP/FOPflash luciferase reporter assay suggested spontaneous activation of β-catenin transactivity in L02 cells expressing HBx/8p11$^{1-674}$ (P=0.010) (FIG. 6G). Our data strongly supports the role for full-length fusion transcript HBx/8p11$^{1-674}$ in the functional advantages observed, by eliminating the possibility of these phenotypes being contributed from the protein translated by either C-terminus truncated HBx$^{1-297}$, HBx/8p11$^{1-312}$* or generally non-transcribing 8p11 human repetitive sequences. It is also likely that HBx/8p11$^{1-674}$ exerts its functional phenotypes as a non-protein coding RNA transcript.

HBx/8p11 Transgene Increases Susceptibility to DEN-Induced Hepatocarcinogenesis

Gross morphology of liver in HBx/8p11 TG mice induced more tumors when compared with wild type mice upon DEN induced HCC development at 8 months, with hematoxylin and eosin (H&E) staining confirmed the presence of tumors. HBx/8p11 TG mice was significantly more susceptible to more DEN induced tumor (mean=12.86, P=0.0025) than wild type mice (mean=3.889).

All patents, patent applications, and other publications, including GenBank Accession Numbers, cited in this application are incorporated by reference in the entirety for all purposes.

Informal Sequence Listing (297 nt, corresponding to 1326-1622 nt of HBV genome, NC_003977)
SEQ ID NO: 1
CGG AAC CGA CAA CTC TGT TGT CCT CTC TCG AAA ATA CAC CTC CTT TCC ATG

GCT GCT AGG GTG TGC TGC CAA CTG GAT CCT GCG CGG GAC GTC CTT TGT CTA

CGT CCC GTC GGC GCT GAA TCC CGC GGA CGA CCC GTC TCG GGG CCG TTT GGG

ACT CTA CCG TCC CCT TCT TCG TCT GCC GTT CCG GCC GAC CAC GGG GCG CAC

CTC TCT TTA CGC GGT CTC CCC GTC TGT GCC TTC TCA TCT GCC GGA CCG TGT

GCA CTT CGC TTC ACC TCT GCA CGT CGC ATG GAA ACC ACC GTG (400 nt, human genomic sequence at 8p11 region, 41,612,680 to 41,613,080 nt)
SEQ ID NO: 2
ATACAAAAATTAGACGGGCATAGTGGCGGGTGCCTGTAGTCCCAGCTACT

CGGGAGGCTGAGGCAGGAGAATTGCTTGAGCCTGGGAGGCAGAGGTTGCA

GTGAGCTGAGATTGCACCACTGCACTCTGGCCTGGGTGACAGAACGAGAC

TCTGTCTCAGGAAACAAAACAAAACAAAAACCCCCAAAACAAATCAAACA

CTTCGATAGCAAGAAAACAAATAACCCAATTAAAAAATGGGCCTGGGACG

TGAATAGACATTTCTGAAAATAAGACATACAAATGACCAACAGACATGAA

AAAACAATGCTCCACCTCACTAATCATTAGGGAATGCAAATTAAAACCAC

AATGAGCTATCGCCTCGCACCTGTCAGAATGACTGTTATCAAAAATGCAA

G (380 nt, human genomic sequence at 8p11 region, 41,613,080 to 41,613,459 nt)
SEQ ID NO: 3
GTG TTG TTG AGG ATG TGA AGT AAA GAA AAC CCT GCC TGC CTC TTG GTA GGA

ATG TAA ATT AGA TTA GCT ATT GTG GAA AAC AGC ATG GAG ATT CCT AAA ACT

AAA ACC AGA GCT TCC ATA TGA TCC AGC AGT CCC CTA CTA GGA AAG GAA

ATC AAT ATA TCA AAG AGA TAC CTG CAC TCC CAT GTT TAT TGC AGC ACT ATT

CAC AAT GAC CAA GAT TTG GAA TCA ACT TGT GTC CAT CAT AGA TGA GTA GAT

AAG GAA AAT GTG GTA TAT GTC ATC ATG GAA TAT TAT TCG GTG TTA AAA AAG

AAG GAA ATC CTG TCA TTT GCG ACA TCG TGG ATG GAA TCG AAG AAC ATT ATG

CTA AGT AAA ATA AAT CAA TCA CAG GA (674 nt, HBx/8p11 mRNA coding sequence, SEQ ID NO: 1 + SEQ ID NO: 3. Underlined GTG indicates shared tri-nucleotides between SEQ ID NO: 1 and SEQ ID NO: 3)
SEQ ID NO: 4
CGG AAC CGA CAA CTC TGT TGT CCT CTC TCG AAA ATA CAC CTC CTT TCC ATG

GCT GCT AGG GTG TGC TGC CAA CTG GAT CCT GCG CGG GAC GTC CTT TGT CTA

CGT CCC GTC GGC GCT GAA TCC CGC GGA CGA CCC GTC TCG GGG CCG TTT GGG

ACT CTA CCG TCC CCT TCT TCG TCT GCC GTT CCG GCC GAC CAC GGG GCG CAC

CTC TCT TTA CGC GGT CTC CCC GTC TGT GCC TTC TCA TCT GCC GGA CCG TGT

GCA CTT CGC TTC ACC TCT GCA CGT CGC ATG GAA ACC ACC GTG TTG TTG AGG

ATG TGA AGT AAA GAA AAC CCT GCC TGC CTC TTG GTA GGA ATG TAA ATT AGA

TTA GCT ATT GTG GAA AAC AGC ATG GAG ATT CCT AAA ACT AAA ACC AGA GCT

TCC ATA TGA TCC AGC AGT CCC CTA CTA GGA AAG GAA ATC AAT ATA TCA AAG

AGA TAC CTG CAC TCC CAT GTT TAT TGC AGC ACT ATT CAC AAT GAC CAA GAT

TTG GAA TCA ACT TGT GTC CAT CAT AGA TGA GTA GAT AAG GAA AAT GTG GTA

-continued

TAT GTC ATC ATG GAA TAT TAT TCG GTG TTA AAA AAG AAG GAA ATC CTG TCA

TTT GCG ACA TCG TGG ATG GAA TCG AAG AAC ATT ATG CTA AGT AAA ATA AAT

CAA TCA CAG GA (anti-sense RNA sequence)                                    SEQ ID NO: 5
ACCACCGUGUUGUUGAGGAUGUGAA (anti-sense DNA sequence encoding SEQ ID NO: 5)              SEQ ID NO: 6
ACCACCGTGTTGTTGAGGATGTGAA

---

What is claimed is:

1. An isolated polynucleotide comprising the nucleotide sequence of SEQ ID NO:4 or the nucleotide sequence complementary to SEQ ID NO:4, wherein the polynucleotide is attached to a detectable moiety, and wherein the detectable moiety is not one or more nucleotides.

2. The polynucleotide of claim 1, which is a DNA.

3. The polynucleotide of claim 1, which is an RNA.

4. A kit for assessing the presence or risk of HBx/8p11-positive human hepatocellular carcinoma (HCC) in a subject, comprising the polynucleotide of claim 1.

5. The kit of claim 4, further comprising two oligonucleotide primers, which hybridize with (1) SEQ ID NO:2 and SEQ ID NO:3, respectively; or (2) complement of SEQ ID NO:2 and complement of SEQ ID NO:3, respectively.

6. The kit of claim 4, further comprising an instruction manual.

* * * * *